US011970718B2

(12) United States Patent
Lodish et al.

(10) Patent No.: US 11,970,718 B2
(45) Date of Patent: Apr. 30, 2024

(54) NUCLEIC ACID LOADED EXTRACELLULAR VESICLES

(71) Applicant: Carmine Therapeutics Pte. Ltd., Singapore (SG)

(72) Inventors: Harvey Lodish, Brookline, MA (US); Ronne Yeo, Singapore (SG); Waqas Muhammad Usman, Kowloon (HK); Tenzin Gocha, Singapore (SG)

(73) Assignee: Carmine Therapeutics Pte. Ltd., Singapore (SG)

( * ) Notice: Subject to any disclaimer, the term of this patent is extended or adjusted under 35 U.S.C. 154(b) by 0 days.

(21) Appl. No.: 17/146,902

(22) Filed: Jan. 12, 2021

(65) Prior Publication Data

US 2021/0214217 A1    Jul. 15, 2021

Related U.S. Application Data

(60) Provisional application No. 62/981,880, filed on Feb. 26, 2020, provisional application No. 62/960,569, filed on Jan. 13, 2020.

(51) Int. Cl.
| | | |
|---|---|---|
| *A61K 48/00* | (2006.01) | |
| *A61K 9/127* | (2006.01) | |
| *A61K 35/18* | (2015.01) | |
| *B82Y 5/00* | (2011.01) | |
| *C12N 9/16* | (2006.01) | |
| *C12N 15/113* | (2010.01) | |
| *C12N 15/88* | (2006.01) | |

(52) U.S. Cl.
CPC .............. *C12N 9/16* (2013.01); *A61K 9/1271* (2013.01); *A61K 35/18* (2013.01); *A61K 48/0058* (2013.01); *A61K 48/0091* (2013.01); *B82Y 5/00* (2013.01); *C12N 15/113* (2013.01); *C12N 15/88* (2013.01); *C12N 2310/14* (2013.01); *C12N 2310/532* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 5,785,992 | A * | 7/1998 | Ansell .................... | C12N 15/88 424/450 |
| 8,329,161 | B2 | 12/2012 | Huang | |
| 9,085,778 | B2 | 7/2015 | Lotvall et al. | |
| 9,629,929 | B2 | 4/2017 | Lotvall et al. | |
| 10,709,797 | B2 * | 7/2020 | Le ........................ | A61K 48/0008 |
| 2009/0274630 | A1 | 11/2009 | Huang | |
| 2010/0104507 | A1 | 4/2010 | Klinman et al. | |
| 2014/0030697 | A1 | 1/2014 | Ploegh et al. | |
| 2016/0331686 | A1 | 11/2016 | Polach et al. | |
| 2019/0054192 | A1 * | 2/2019 | Le ........................ | A61K 48/0041 |
| 2020/0138987 | A1 | 5/2020 | Ahn et al. | |
| 2020/0230259 | A1 | 7/2020 | Le et al. | |
| 2021/0353769 | A1 | 11/2021 | Shi et al. | |
| 2021/0355492 | A1 | 11/2021 | Shi et al. | |
| 2022/0002730 | A1 | 1/2022 | Kortylewski et al. | |
| 2023/0050813 | A1 | 2/2023 | Gocha et al. | |
| 2023/0121065 | A1 * | 4/2023 | Le ........................ | C12N 15/88 424/93.2 |

FOREIGN PATENT DOCUMENTS

| | | |
|---|---|---|
| CN | 109402176 A | 3/2019 |
| CN | 109750068 A | 5/2019 |
| CN | 110652492 A | 1/2020 |
| RU | 2608509 C1 | 1/2017 |
| WO | WO 2010/119256 A1 | 10/2010 |
| WO | WO 2014/183066 A2 | 11/2014 |
| WO | WO 2014/183071 A2 | 11/2014 |
| WO | WO 2015/002956 A1 | 1/2015 |
| WO | WO 2015/069897 A1 | 5/2015 |
| WO | WO 2016/014553 A1 | 1/2016 |
| WO | WO 2016/187717 A1 | 1/2016 |
| WO | WO 2017/054085 A1 | 4/2017 |
| WO | WO 2018/062973 A1 | 4/2018 |
| WO | WO 2020/060479 A1 | 3/2020 |
| WO | WO 2020/060496 A1 | 3/2020 |
| WO | WO 2021/076973 A1 | 4/2021 |
| WO | WO 2021/145821 A1 | 7/2021 |
| WO | WO 2021/180237 A1 | 9/2021 |
| WO | WO 2021/194425 A1 | 9/2021 |
| WO | WO 2021/228832 A1 | 11/2021 |
| WO | WO 2022/031237 A1 | 2/2022 |
| WO | WO 2023/172208 A1 | 9/2023 |

OTHER PUBLICATIONS

Genomic library—Wikipedia; pp. 1-8; downloaded on Jul. 1, 2021.*
Lee et al SS 30 LB: Symposium Session 30—Late Breaking Abstracts Chair: Lei Zheng Location: Room 6 ISEV 2018 abstract book; p. 265.*
Chen et al Research Article Intracellular production of DNA enzyme by a novel single-stranded DNA expression vector Gene Therapy (2003) 10, 1776-1780.*
MC-Easy™ Minicircle DNA Production Kit (with Competent Cells; pp. 1-6; downloaded Oct. 13, 2021.*
Polyethylenimine HCI MAX, Linear, MW 40000, Transfection Grade (PEI MAX 40K) | . . . pp. 1-7; downloaded Oct. 15, 2021.*
Pandey et al ; 2016; Materials Science and Engineering C 68 pp. 904-918.*
Pinnapireddy Composite liposome-PEI/nucleic acid lipopolyplexes for safe and efficient gene delivery and gene knockdown Colloids and Surfaces B: Biointerfaces 158 (2017) 93-101.*
Godby et al Size matters: Molecular weight affects the efficiency of poly(ethylenimine) as a gene delivery vehicle Journal of Biomedical Materials Research 45, 268-275, 1999.*

(Continued)

*Primary Examiner* — Maria G Leavitt
(74) *Attorney, Agent, or Firm* — Wolf, Greenfield & Sacks, P.C.

(57) ABSTRACT

An extracellular vesicle loaded with a nucleic acid cargo and method for preparing the loaded vesicle is disclosed.

22 Claims, 15 Drawing Sheets

(56) References Cited

OTHER PUBLICATIONS

Sahoo et al., Jun. 21, 2018 Nature, Home Research Industry Special Resource Conference Exosome Home Forum. pp. 1-11. A machine translated copy of the article is provided.*
Wang et al Transfection Efficiency Evaluation and Endocytosis Exploration of Different Polymer Condensed Agents DNA and Cell Biology vol. 38, No. 10, 2019 pp. 1048-1055.*
Cai et al Effect of Chain Length on Cytotoxicity and Endocytosis of Cationic Polymers Macromolecules 2011, 44, 2050-2057.*
Rekha et al Acta Biomaterialia 2011 pp. 370-379 Hemocompatible pullulan-polyethyleneimine conjugates for liver cell gene delivery: In vitro evaluation of cellular uptake, intracellular trafficking and transfection efficiency.*
Canton et al., Chem. Soc. Rev., 2012, 41, 2718-2739 Endocytosis at the nanoscale.*
Zhang et al., 2019, The biology and therapeutic applications of red blood cell extracellular vesicles; Chapter 8 pp. 1-15.*
Simões et al., 2005, Cationic liposomes for gene delivery Expert Opinion on Drug Delivery, 2:2, 237-254.*
International Search Report and Written Opinion for Application No. PCT/SG2021/050020, dated Mar. 19, 2021.
[No Author Listed], Exo-Fect™ Exosome Transfection. Exo-Fect™ Exosome Tranfection Kits. Create novel "FedExosomes". Retrieved from web.archive.org/web/20160720184745/https://www.stratech.co.uk/sbi/exo-fect-exosome-transfection. Jul. 20, 2016. 6 pages.
Alvarez-Erviti et al., Delivery of siRNA to the mouse brain by systemic injection of targeted exosomes. Nat Biotechnol. Apr. 2011;29(4):341-5. doi: 10.1038/nbt.1807. Epub Mar. 20, 2011. Supplemental information, 14 pages.
Aqil et al., Milk exosomes—Natural nanoparticles for siRNA delivery. Cancer Lett. May 1, 2019;449:186-195. doi: 10.1016/j.canlet.2019.02.011. Epub Feb. 13, 2019.
El-Andaloussi et al., Exosome-mediated delivery of siRNA in vitro and in vivo. Nat Protoc. Dec. 2012;7(12):2112-26. doi: 10.1038/nprot.2012.131. Epub Nov. 15, 2012.
Ha et al., Exosomes as therapeutic drug carriers and delivery vehicles across biological membranes: current perspectives and future challenges. Acta Pharm Sin B. Jul. 2016;6(4):287-96. doi: 10.1016/j.apsb.2016.02.001. Epub Mar. 8, 2016.
Kamerkar et al., Exosomes facilitate therapeutic targeting of oncogenic KRAS in pancreatic cancer. Nature. Jun. 22, 2017;546(7659):498-503. doi: 10.1038/nature22341. Epub Jun. 7, 2017. Supplemental Information, 18 pages.
Kanada et al., Differential fates of biomolecules delivered to target cells via extracellular vesicles. Proc Natl Acad Sci U S A. Mar. 24, 2015;112(12):E1433-42. doi: 10.1073/pnas.1418401112. Epub Feb. 23, 2015.
Kanada et al., Microvesicle-Mediated Delivery of Minicircle DNA Results in Effective Gene-Directed Enzyme Prodrug Cancer Therapy. Mol Cancer Ther. Dec. 2019;18(12):2331-2342. doi: 10.1158/1535-7163.MCT-19-0299. Epub Aug. 26, 2019. Author Manuscript, 32 pages.
Kooijmans et al., Electroporation-induced siRNA precipitation obscures the efficiency of siRNA loading into extracellular vesicles. J Control Release. Nov. 28, 2013;172(1):229-238. doi: 10.1016/j.jconrel.2013.08.014. Epub Aug. 29, 2013.
Lamichhane et al., Exogenous DNA Loading into Extracellular Vesicles via Electroporation is Size-Dependent and Enables Limited Gene Delivery. Mol Pharm. Oct. 5, 2015;12(10):3650-7. doi: 10.1021/acs.molpharmaceut.5b00364. Epub Sep. 23, 2015.
Luan et al., Engineering exosomes as refined biological nanoplatforms for drug delivery. Acta Pharmacol Sin. Jun. 2017;38(6):1-10. doi: 10.1038/aps.2017.12. Epub Apr. 10, 2017.
Lv et al., Toxicity of cationic lipids and cationic polymers in gene delivery. J Control Release. Aug. 10, 2006;114(1):100-9. doi: 10.1016/j.jconrel.2006.04.014. Epub May 13, 2006.
Nguyen et al., Characterization of Microvesicles Released from Human Red Blood Cells. Cell Physiol Biochem. 2016;38(3):1085-99. doi: 10.1159/000443059. Epub Mar. 4, 2016.

Nguyen et al., Microvesicles released from human red blood cells: Properties and potential applications. Novel Implications of Exosomes in Diagnosis and Treatment of Cancer and Infectious Diseases. Jul. 12, 2017;12:137-61. http://dx.doi.org/10.5772/intechopen.69599.
Penguin, Another gene therapy company based on extracellular vesicles announced the esstablishment—Carmine Therapeutics. Retrieved on Feb. 16, 2021 from https://www.exosomemed.com/6218.html. Sep. 5, 2019. 8 pages.
Prevette et al., Polycation-induced cell membrane permeability does not enhance cellular uptake or expression efficiency of delivered DNA. Mol Pharm. Jun. 7, 2010;7(3):870-83. doi: 10.1021/mp100027g. Erratum in: Mol Pharm. Dec. 6, 2010;7(6):2370.
Sonawane et al., Chloride accumulation and swelling in endosomes enhances DNA transfer by polyamine-DNA polyplexes. J Biol Chem. Nov. 7, 2003;278(45):44826-31. doi: 10.1074/jbc.M308643200. Epub Aug. 27, 2003.
Usman et al., Efficient RNA drug delivery using red blood cell extracellular vesicles. Nat Commun. Jun. 15, 2018;9(1):2359(1-15). doi: 10.1038/s41467-018-04791-8.
Wahlgren et al., Plasma exosomes can deliver exogenous short interfering RNA to monocytes and lymphocytes. Nucleic Acids Res. Sep. 1, 2012;40(17):e130(1-12). doi: 10.1093/nar/gks463. Epub May 22, 2012.
Wang et al., ARMMs as a versatile platform for intracellular delivery of macromolecules. Nat Commun. Mar. 6, 2018;9(1):960(1-7). doi: 10.1038/s41467-018-03390-x.
Yang et al., Large-scale generation of functional mRNA-encapsulating exosomes via cellular nanoporation. Nat Biomed Eng. Jan. 2020;4(1):69-83. doi: 10.1038/s41551-019-0485-1. Epub Dec. 16, 2019. Erratum in: Nat Biomed Eng. Aug. 2021;5(8):944-945.
Zhang et al. The biology and therapeutic applications of red blood cell extracellular vesicles. Erythrocyte. Oct. 23, 2019; 121: 1-16. DOI: http://dx.doi.org/10.5772/intechopen.81758.
François-Martin et al., Actual fusion efficiency in the lipid mixing assay—Comparison between nanodiscs and liposomes. Sci Rep. Mar. 7, 2017;7:43860. doi: 10.1038/srep43860. PMID: 28266607; PMCID: PMC5339690.
Vorselen et al., The fluid membrane determines mechanics of erythrocyte extracellular vesicles and is softened in hereditary spherocytosis. Nat Commun. Nov. 23, 2018;9(1):4960. doi: 10.1038/s41467-018-07445-x. PMID: 30470753; PMCID: PMC6251882.
[No Author Listed] AMA Style Insider (Sep. 2012) downloaded from https://amastyleinsider.com/2012/09/14/around-about-approximately/ on Mar. 24, 2023.
[No Author Listed] e.insights (Jun. 2014) downloaded from https://www.editage.com/insights/scientific-writing-difference-in-meaning-of-about-around-and-approximately on Mar. 24, 2023.
Abu-Dahab et al., Lectin-functionalized liposomes for pulmonary drug delivery: effect of nebulization on stability and bioadhesion. European Journal of Pharmaceutical Sciences, Jul. 10, 2001;14(1):37-46.
Chang et al., Homologous RBC-derived vesicles as ultrasmall carriers of iron oxide for magnetic resonance imaging of stem cells. Nanotechnology. Jun. 11, 2010;21(23):235103. doi: 10.1088/0957-4484/21/23/235103. Epub May 17, 2010.
City University of Hong Kong, Cancer breakthrough for drug delivery. South China Morning Post. Published Oct. 3, 2018. Retrieved from https://www.scmp.com/presented/news/hong-kong/topics/treating-cancer-cityus-breakthroughtechnologies/article/2165117 on Dec. 11, 2018. 4 pages.
Dai et al., Broadening the scope of sortagging. RSC Adv. Feb. 6, 2019;9(9):4700-4721. doi: 10.1039/c8ra06705h.
Huang et al., Genetically engineered red cells expressing single domain camelid antibodies confer long-term protection against botulinum neurotoxin. Nat Commun. Sep. 4, 2017;8(1):423. doi: 10.1038/s41467-017-00448-0.
Lai et al., Dynamic biodistribution of extracellular vesicles in vivo using a multimodal imaging reporter. ACS Nano. Jan. 28, 2014;8(1):483-494. doi: 10.1021/nn404945r. Epub Jan. 9, 2014.
Le, Behind the Paper: Harnessing red blood cell vesicles for gene therapies. Retrieved from https://bioengineeringcommunity.nature.com on Dec. 11, 2018. 6 pages.

(56) References Cited

OTHER PUBLICATIONS

Luan et al., Base-by-base ratcheting of single stranded DNA through a solid-state nanopore. Phys Rev Lett. Jun. 11, 2010;104(23):238103. doi: 10.1103/PhysRevLett.104.238103. Epub Jun. 10, 2010.

McPeck et al., Factors Determining Continuous Infusion Aerosol Delivery During Mechanical Ventilation. Respiratory Care. Apr. 2021;66(4):573-81.

Meyer et al., Novel Developments to Enable Treatment of CNS Diseases with Targeted Drug Delivery. Pharmaceutics. Mar. 29, 2023;15(4):1100, 25 pages.

Muzykantov, Drug delivery by red blood cells: vascular carriers designed by mother nature. Expert Opin Drug Deliv. Apr. 2010;7(4):403-27. doi: 10.1517/17425241003610633.

Pham et al., Covalent conjugation of extracellular vesicles with peptides and nanobodies for targeted therapeutic delivery. J Extracell Vesicles. Feb. 2021;10(4):e12057. doi: 10.1002/jev2.12057. Epub Feb. 16, 2021.

Pham et al., Red blood cell extracellular vesicles as robust carriers of RNA-based therapeutics. Cell Stress. Aug. 30, 2018;2(9):239-241. doi: 10.15698/cst2018.09.155.

Pishesha et al., Engineered erythrocytes covalently linked to antigenic peptides can protect against autoimmune disease. Proc Natl Acad Sci U S A. Mar. 21, 2017;114(12):3157-3162. doi: 10.1073/pnas.1701746114. Epub Mar. 7, 2017. Erratum in: Proc Natl Acad Sci U S A. Apr. 25, 2017;114(17 ):E3583. Dhesycka, Rhogerry [corrected to Deshycka, Rhogerry].

Popp et al., Sortagging: a versatile method for protein labeling. Nat Chem Biol. Nov. 2007;3(11):707-8. doi: 10.1038/nchembio.2007.31. Epub Sep. 23, 2007.

Prudent et al., Differences between calcium-stimulated and storage-induced erythrocyte-derived microvesicles. Transfus Apher Sci. Oct. 2015;53(2):153-8. doi: 10.1016/j.transci.2015.10.012. Epub Oct. 27, 2015.

Raimondo et al., Poster Session 4—Evs as drug delivery system for antitumoral therapies and vaccination, Abstract PW4.11, The Fifth International Meeting of ISEV, ISEV2016, Rotterdam, The Netherlands, May 4-7, 2016. J Extracell Vesicles. May 30, 2016;5:31552. doi: 10.3402/jev.v5.31552.

Shi et al., Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.

Stern et al., The effects of jet nebulisation on cationic liposome-mediated gene transfer in vitro. May 21, 1998;5(5):583-93.

Sunkara et al., Emerging techniques in the isolation and characterization of extracellular vesicles and their roles in cancer diagnostics and prognostics. Analyst. Jan. 21, 2016;141(2):371-81. doi: 10.1039/c5an01775k.

Swee et al., One-step enzymatic modification of the cell surface redirects cellular cytotoxicity and parasite tropism. ACS Chem Biol. Feb. 20, 2015;10(2):460-5. doi: 10.1021/cb500462t. Epub Nov. 10, 2014.

Tabata et al., Development of a Sortase A-mediated Peptide-labeled Liposome Applicable to Drug-delivery Systems. Anticancer Res. Aug. 2015;35(8):4411-7.

Tian et al., Surface functionalized exosomes as targeted drug delivery vehicles for cerebral ischemia therapy. Biomaterials. Jan. 2018; 150:137-149. doi: 10.1016/j.biomaterials.2017.10.012. Epub Oct. 4, 2017.

Vader et al., New considerations in the preparation of nucleic acid-loaded extracellular vesicles. Ther Deliv. Feb. 2014;5(2):105-7. doi: 10.4155/tde.13.142.

Van Niel et al., Shedding light on the cell biology of extracellular vesicles. Nat Rev Mol Cell Biol. Apr. 2018;19(4):213-228. doi: 10.1038/nrm.2017.125. Epub Jan. 17, 2018.

Vogel et al., Comparison of the Pulmonary Distribution and Efficacy of Antibodies Given to Mice by Intratracheal Instillation or Aerosol Inhalation. Laboratory Animal Science. Oct. 1996;46(5):516-23.

Warashina et al., A lipid nanoparticle for the efficient delivery of siRNA to dendritic cells. J Control Release. Mar. 10, 2016;225:183-91. doi: 10.1016/j.jconrel.2016.01.042. Epub Jan. 26, 2016.

Webber et al., How pure are your vesicles? J Extracell Vesicles. Jan. 10, 2013;2. doi: 10.3402/jev.v210.19861.

Xu et al., Extracellular vesicle isolation and characterization: toward clinical application. J Clin Invest. Apr. 1, 2016;126(4):1152-62. doi: 10.1172/JCI81129. Epub Apr. 1, 2016.

Zhang et al., Upregulation of microRNA-125b contributes to leukemogenesis and increases drug resistance in pediatric acute promyelocytic leukemia. Mol Cancer. Sep. 1, 2011;10:108. doi: 10.1186/1476-4598-10-108.

Zhupanyn et al., Extracellular vesicle (ECV)-modified polyethylenimine (PEI) complexes for enhanced siRNA delivery in vitro and in vivo. J Control Release. Mar. 10, 2020;319:63-76. doi: 10.1016/j.jconrel. 2019.12.032. Epub Dec. 19, 2019.

Yang, Y. et al., Influence of Cell Morphology on Mesenchymal Stem Cell Transfection, ACS Appl. Mater Interfaces, 11:1932-1941 (2019).

* cited by examiner

NUCLEIC ACID LOADED EXTRACELLULAR VESICLES

This application claims priority from U.S. 62/960,569 filed 13 Jan. 2020 and U.S. 62/981,880 filed 26 Feb. 2020, the contents and elements of which are herein incorporated by reference for all purposes.

FIELD OF THE INVENTION

The present invention relates to extracellular vesicles and particularly, although not exclusively, to extracellular vesicles derived from red blood cells.

BACKGROUND

Extracellular vesicles (EVs) are cell-derived lipid membrane-bound vesicles that mediate the transfer of biomolecules between cells. It is widely accepted that there are 2 classes of EVs, namely 1) exosomes which are generated from the inward budding of the endosomal membrane, forming intraluminal vesicles in multivesicular bodies that would eventually fuse with the plasma membrane and release exosomes into the extracellular space; and 2) microvesicles, which are formed by directly budding off from the plasma membrane. Typically, exosomes are 30-100 nm in diameter, whereas microvesicles are larger than 100 nm.

Because of their natural ability to transport large macromolecules across the cell membrane, EVs have been proposed as drug delivery vehicles for the transport of small molecules, proteins and nucleic acids that include short RNAs like antisense oligonucleotides (ASOs), short interfering RNAs (siRNAs) and microRNAs (miRNAs), long RNAs like messenger RNAs (mRNA), or even double-stranded DNA (dsDNA). EV-mediated delivery of nucleic acids is highly sought after as these macromolecules are promising drug candidates with a potential to treat a wide array of diseases, yet the development of nucleic acids as drugs has been impeded due to several reasons that include their inability to penetrate cell membranes, immunogenicity and vulnerability to nucleases in the systemic circulation. Several other types of delivery vehicles such as lipid nanoparticles and cationic polymers have been used for nucleic acid delivery, but their applications are limited due to liver toxicity and limited extra-hepatic biodistribution.

Loading of nucleic acids in EVs would overcome most of these challenges as EVs are biocompatible, have a unique tropism, and depending on their cellular origin, they pose little toxicity or immunogenicity threat. EVs can either be loaded endogenously through transfecting or overexpressing payloads in the cell source followed by purifying the EVs produced by these cells, or exogenously through direct loading of isolated EVs using mechanical means (i.e. electroporation, sonication, freeze-thaw, cell extrusion) or chemical means (i.e. lipofection or calcium chloride treatment). Based on the literature, most attempts to load nucleic acids involve short RNAs such as siRNA, miRNA and ASOs, and these payloads are loaded through exogenous means, usually electroporation.

Attempts to load nucleic acids larger than 1000 base pairs into extracellular vesicles have met with challenges and are very inefficient (Mol Pharm. 2015 Oct. 5; 12(10): 3650-3657). The size of the payload is the usual limiting factor for exogenous loading of purified EVs (PNAS Mar. 24, 2015 112 (12) E1433-E1442) (Mol Pharm. 2015 Oct. 5; 12(10): 3650-3657). Also, it has not been possible to successfully load large nucleic acids into EVs without causing vesicle aggregation, a loss in yield or function (Mol Pharm. 2015 Oct. 5; 12(10): 3650-3657). As a result, DNA gene expression vectors, which are typically larger than 1000 base pairs in size, are deemed as a challenging cargo for EVs.

Yang et al., (Nature Biomedical Engineering) explain that inserting exogenous nucleic acids, particularly large messenger RNAs, into cell-secreted exosomes leads to low yields. In order to address this issue, they developed a cellular-nanoporation method in which source cells were transfected with plasmid DNAs and subsequently stimulated with a focal and transient electrical stimulus to promote the release of exosomes carrying transcribed mRNAs and targeting peptides, Compared with bulk electroporation and other exosome-production strategies, they reported up to 50-fold more exosomes and a more than 103-fold increase in exosomal mRNA transcripts, even from cells with low basal levels of exosome secretion.

WO2010/119256 describes electroporation of exosomes with circular and linearized pEGFP-NAD. Electroporation appeared to protect the circular DNA plasmid from DNase I degradation, but not the linear DNA. They achieved inconsistent results and often low level of protection from degradation.

Noting that only small RNAs (siRNA and miRNA) had been successfully loaded into extracellular vesicles, Lamichhane et al. (Exogenous DNA Loading into Extracellular Vesicles via Electroporation is Size-Dependent and Enables Limited Gene Delivery. Mol Pharm. 2015 Oct. 5; 12(10): 3650-3657) investigated loading of DNA into extracellular vesicles from HEK293T cells, HUVEC cells and human mesenchymal stem cells. They determined that loading efficiency and capacity in extracellular vesicles is dependent on DNA size, with linear DNA molecules of less than 1000 bp in length being more efficiently associated with extracellular vesicles compared to larger linear DNAs and plasmid DNAs, in particular noting a "size limitation cutoff in the range of 750-1000 bp".

Usman et al. (Efficient RNA drug delivery using red blood cell extracellular vesicles. Nature Communications Nat Commun 9, 2359 (2018) doi:10.1038/s41467-018-04791-8) describe a strategy to generate large-scale amounts of red blood cell-derived extracellular vesicles for the delivery of RNA.

The present invention has been devised in light of the above considerations.

SUMMARY OF THE INVENTION

The present inventors have developed a method for loading cargo into extracellular vesicles. In particular, the method allows nucleic acid cargo such as DNA to be loaded into extracellular vesicles such as red blood cell-derived extracellular vesicles or exosomes. The resultant loaded extracellular vesicles are useful in therapy and research, for delivering the cargo to target cells in vitro and in vivo.

In one aspect of the present disclosure, there is provided an extracellular vesicle loaded with a cargo or a population of such extracellular vesicles. The cargo is preferably a nucleic acid. The nucleic acid may be a DNA, an RNA, or other oligonucleotide or polynucleotide. The nucleic acid is most preferably a DNA. The nucleic acid may be circular or circularized, or linear. The nucleic acid may be double or single stranded, preferably double stranded. In some aspects, the nucleic acid is a circularized DNA, such as a DNA minicircle, plasmid or nanoplasmid (Aldevron).

Where the nucleic acid cargo is single stranded it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000, 20000, 21000, 22000, 23000, 24000, 25000, 26000, 27000, 28000, 29000 or 30000 bases. Optionally, wherein the nucleic acid cargo is single stranded DNA (ssDNA) it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000, 20000, 21000, 22000, 23000, 24000, 25000, 26000, 27000, 28000, 29000 or 30000 bases. In preferred embodiments a single stranded nucleic acid cargo may have a minimum length of one of 2000, 2250, 2500, 2750, 3000, 3250, 3500, 3750, 4000, 4250, 4500, 4750, 5000, 6000, 7000, 8000, 9000, 10000 or more than 10000 bases.

Where the nucleic acid cargo is single stranded it may have a length of one of 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, or 7000-11000, bases.

In some embodiments where the nucleic acid cargo is single stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000 or 50000 bases. The single stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, 35000-40000, 35000-45000, 35000-50000, 40000-50000 or 40000-45000 bases.

Where the nucleic acid cargo is double stranded it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000 or 20000 base pairs. Optionally, where the nucleic acid cargo is double stranded it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000 or 20000 base pairs. In preferred embodiments a double stranded nucleic acid cargo may have a minimum length of one of 2000, 2250, 2500, 2750, 3000, 3250, 3500, 3750, 4000, 4250, 4500, 4750, 5000, 6000, 7000, 8000, 9000, 10000 or more than 10000 base pairs.

Where the nucleic acid cargo is double stranded it may have a length of one of 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, 7000-11000, 8000-12000, 8000-13000, 8000-14000, 8000-15000, 9000-13000, 9000-14000, 9000-15000, 9000-16000, 9000-17000, 10000-14000, 10000-15000, 10000-16000, 10000-17000 or 10000-18000 base pairs.

In some embodiments where the nucleic acid cargo is double stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, or 40000 base pairs. The double stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, or 35000-40000 base pairs.

The cargo may preferably be loaded into the lumen of the extracellular vesicle (i.e. lumenal loading). In some cases, some of the cargo is loaded onto the extracellular vesicle (e.g. onto the external surface of membrane of the extracellular vesicle). Cargo molecules loaded onto the external surface of the membrane of the extracellular vesicle may be removed by contacting the vesicle with a nuclease, e.g. a DNase or RNase.

The extracellular vesicle may be a microvesicle or an exosome. Although the extracellular vesicle may be derived from any suitable cell, extracellular vesicles derived from red blood cells (RBCs) are particularly preferred.

Extracellular vesicles according to the present disclosure may be provided in isolated form.

The present disclosure further provides a composition comprising extracellular vesicles loaded with a nucleic acid cargo. In such compositions, the extracellular vesicles may comprise an average of at least 1.0, 2.0, 3.0, 4.0 or more nucleic acid molecules per vesicle.

In another aspect of the present disclosure a red blood cell extracellular vesicle (RBCEV) loaded with a DNA cargo is provided.

In one embodiment an isolated red blood cell extracellular vesicle (RBCEV) containing in the lumen of the RBCEV at least one DNA cargo is provided.

The DNA cargo may be single stranded or double stranded.

Where the DNA cargo is single stranded DNA (ssDNA) it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000, 20000, 21000, 22000, 23000, 24000, 25000, 26000, 27000, 28000, 29000 or 30000 bases. Optionally, where the DNA cargo is single stranded DNA (ssDNA) it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000, 20000, 21000, 22000, 23000, 24000, 25000, 26000, 27000, 28000, 29000 or 30000 bases. In preferred embodiments a single stranded DNA cargo may have a minimum length of one of 2000, 2250, 2500, 2750, 3000, 3250, 3500, 3750, 4000, 4250, 4500, 4750, 5000, 6000, 7000, 8000, 9000, 10000 or more than 10000 bases.

Where the DNA cargo is single stranded DNA (ssDNA) it may have a length of one 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, or 7000-11000, bases.

In some embodiments where the nucleic acid cargo is single stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000 or 50000 bases. The single stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, 35000-40000, 35000-45000, 35000-50000, 40000-50000, or 40000-45000 bases.

Where the DNA cargo is double stranded DNA (dsDNA) it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750, 11000, 12000, 13000, 14000, 15000, 16000, 17000, 18000, 19000 or 20000 base pairs. Optionally, where the DNA cargo is double stranded DNA (dsDNA) it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750 11000, 12000, 13000, 14000, 15000, 16000, 17000, 18000, 19000 or 20000 base pairs. In preferred embodiments a double stranded DNA cargo may have a minimum length of one of 2000, 2250, 2500, 2750, 3000, 3250, 3500, 3750, 4000, 4250, 4500, 4750, 6000, 7000, 8000, 9000, 10000 or more than 10000 base pairs.

Where the DNA cargo is double stranded DNA (dsDNA) it may have a length of one 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, 7000-11000, 8000-12000, 8000-13000, 8000-14000, 8000-15000, 9000-13000, 9000-14000, 9000-15000, 9000-16000, 9000-17000, 10000-14000, 10000-15000, 10000-16000, 10000-17000 or 10000-18000 base pairs.

In some embodiments where the nucleic acid cargo is double stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, or 40000 base pairs. The double stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, or 35000-40000 base pairs.

The DNA cargo may be an expression vector comprising a gene encoding a protein or peptide.

The DNA cargo may be circular (e.g. a minicircle or plasmid) or linear. The DNA cargo may be in the lumen of the RBCEV. The RBCEV is preferably derived or obtained from human or mammalian red blood cells. The RBCEV may be isolated.

In a related aspect of the present disclosure an isolated red blood cell extracellular vesicle (RBCEV) containing in the lumen of the RBCEV at least one nucleic acid (preferably DNA) cargo (as described herein) is provided.

Also provided is a population of isolated red blood cell extracellular vesicles (RBCEVs) in which, on average, each RBCEV is loaded with at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 or more nucleic acid (preferably DNA) cargoes (as described herein). Also provided is a population of isolated red blood cell extracellular vesicles (RBCEVs) containing, on average, at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 or more nucleic acid (preferably DNA) cargoes (as described herein) in the lumen of each RBCEV.

In a related aspect of the present disclosure a composition comprising a plurality of RBCEVs or population of RBCEVs as described herein is provided. In the composition, on average, each RBCEV may be loaded with at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 or more DNA cargoes. In the composition, on average each RBCEV may be loaded with 1.0 to 4.0 DNA cargoes, or one of 0.1 to 1.0, 0.5 to 1.0, 0.5 to 1.5, 0.5 to 2.0, 0.5 to 2.5, 0.5 to 3.0, 0.5 to 3.5, 0.5 to 4.0, 1.0 to 1.5, 1.0 to 2.0, 1.0 to 2.5, 1.0 to 3.0, 1.0 to 3.5, 1.0 to 4.0, 1.5 to 2.0, 1.5 to 2.5, 1.5 to 3.0, 1.5 to 3.5, 1.5 to 4.0, 2.0 to 2.5, 2.0 to 3.0, 2.0 to 3.5, 2.0 to 4.0, 2.5 to 3.0, 2.5 to 3.5, 2.5 to 4.0, 3.0 to 3.5, 3.0 to 4.0, or 3.5 to 4.0 or more cargoes. The average may be a mean average.

The composition may be a pharmaceutical composition or medicament, and may further comprise a pharmaceutically acceptable carrier, diluent, excipient or stabiliser.

Extracellular vesicles described herein may be useful in therapy, particularly gene therapy, for delivering nucleic acids to a target cell to cause expression of a gene in that target cell.

In another aspect of the present disclosure a method of treating a subject in need of treatment is provided, the method comprising administering to the subject a therapeutically effective amount of an extracellular vesicle, preferably an RBCEV, as described herein or a composition comprising a plurality of extracellular vesicles, preferably RBCEVs, as described herein, thereby treating the subject.

In another aspect of the present disclosure an extracellular vesicle, preferably an RBCEV, or composition comprising a plurality of extracellular vesicles, preferably RBCEVs, as described herein, is provided for use in a method of treating a disease in a subject.

In another aspect of the present disclosure the use of one or a plurality of extracellular vesicles as described herein, preferably one or a plurality of RBCEVs as described herein, in the manufacture of a pharmaceutical composition or medicament for use in a method of treating a disease in a subject is provided.

The subject may be a subject in need of treatment. The method of treating a subject may involve treatment of a disease in the subject by expression of a protein or peptide from a gene sequence of the DNA cargo. The treatment may comprise prevention and/or amelioration of the disease.

In another aspect of the present disclosure a method for loading an extracellular vesicle with a nucleic acid cargo, and an extracellular vesicle loaded (or prepared or obtained by) using such a method is provided.

The method is a chemical transfection method. Such methods may involve contacting the nucleic acid with transfection reagent, optionally allowing formation of nucleic acid/transfection reagent complexes; incubating the nucleic acid and transfection reagent with an extracellular vesicle under conditions sufficient for the extracellular vesicle to be loaded with the nucleic acid; and optionally washing the loaded extracellular vesicle. In certain methods, nucleic acid and transfection reagent are incubated with the extracellular vesicle more than once (i.e. the step of incubating the nucleic acid and transfection reagent with the extracellular vesicle is repeated at least once).

In preferred methods, the transfection reagent is a Linear Polyethylenimine Hydrochloride (e.g. of MW 25000 Da or MW 40,000 Da).

Certain methods described herein comprise the step of removing nucleic acid cargo not contained within the lumen of the extracellular vesicle. Removing nucleic acid cargo not contained within the lumen of the extracellular vesicle may comprise contacting the loaded extracellular vesicle with a nuclease, e.g. a DNase or RNase. The loaded extracellular vesicle may be contacted with heparin prior to contact with the nuclease.

In the methods for loading an extracellular vesicle described herein, the nucleic acid cargo may comprise a nucleic acid molecule as described herein. In some preferred embodiments, the extracellular vesicle to be loaded is a red blood cell extracellular vesicle. In other embodiments, the extracellular vesicle is an exosome.

Accordingly, in one aspect of the present disclosure a method for loading an extracellular vesicle with a nucleic acid cargo is provided, the method comprising:
  a. providing a nucleic acid to be loaded into an extracellular vesicle;
  b. contacting or incubating the nucleic acid with an extracellular vesicle in the presence of a transfection reagent under conditions sufficient, and optionally for suitable amount of time, for the extracellular vesicle to be loaded with the nucleic acid; and
  c. optionally washing the loaded extracellular vesicle.

In preferred embodiments the extracellular vesicle is a red blood cell extracellular vesicle, or a population of red blood cell extracellular vesicles.

The method may comprise repeating step b, one, two, three or more times. Step b may be repeated before or after step c by providing more nucleic acid for loading into the extracellular vesicle. The inventors have found that repeating the loading step of contacting or incubating the nucleic acid with an extracellular vesicle in the presence of a transfection reagent improves the amount of nucleic acid loaded to the extracellular vesicles.

In another aspect of the present disclosure a method for loading an extracellular vesicle with a nucleic acid cargo is provided, the method comprising:
  a. providing a nucleic acid to be loaded into an extracellular vesicle;
  b. contacting the nucleic acid with transfection reagent to allow formation of nucleic acid/transfection reagent complexes; and
  c. incubating or contacting the nucleic acid/transfection reagent complexes with an extracellular vesicle under conditions sufficient, and optionally for suitable amount of time, for the extracellular vesicle to be loaded with a nucleic acid/transfection reagent complex; and
  d. optionally washing the loaded extracellular vesicle.

In preferred embodiments the extracellular vesicle is a red blood cell extracellular vesicle, or a population of red blood cell extracellular vesicles.

The method may comprise repeating steps b-d through one, two, three or more cycles. This may involve providing more nucleic acid for loading into the extracellular vesicle. The inventors have found that repeating the loading step of contacting or incubating the nucleic acid with an extracellular vesicle in the presence of a transfection reagent improves the amount of nucleic acid loaded to the extracellular vesicles.

In a related aspect of the present disclosure a method for loading an extracellular vesicle with a nucleic acid cargo is provided, the method comprising:

a. providing a nucleic acid to be loaded into an extracellular vesicle;
b. contacting the nucleic acid with transfection reagent to allow formation of nucleic acid/transfection reagent complexes; and
c. incubating or contacting the nucleic acid/transfection reagent complexes with an extracellular vesicle under conditions sufficient, and optionally for suitable amount of time, for the extracellular vesicle to be loaded with a nucleic acid/transfection reagent complex;
d. optionally washing the loaded extracellular vesicle;
e. contacting the loaded extracellular vesicle with further nucleic acid/transfection reagent complexes; and
f. incubating or contacting the further nucleic acid/transfection reagent complexes with the loaded extracellular vesicle.

The method may comprise repeating steps b-d at least once, before progressing to following steps, e.g. to step e.

In preferred embodiments the extracellular vesicle is a red blood cell extracellular vesicle, or a population of red blood cell extracellular vesicles.

In any of the above methods, the transfection reagent may be a linear polyethylenimine hydrochloride, optionally of MW 25,000 Da or MW 40,000 Da.

The methods may further comprise the step of removing nucleic acid cargo not contained within the lumen of the extracellular vesicle. This may comprise contacting the loaded extracellular vesicle with a nuclease, e.g. an RNase or DNase. The loaded extracellular vesicle may be contacted with heparin prior to contact with the nuclease.

The nucleic acid cargo may comprise nucleic acid molecules, wherein each nucleic acid molecule is single stranded and has a length of at least 250 bases, or at least 2000 bases, or 2000-11000 bases, or more.

The nucleic acid cargo may comprise nucleic acid molecules, wherein each nucleic acid molecule is double stranded and has a length of at least 250 base pairs, or at least 2000 base pairs, or 2000-11000 base pairs, or more.

The nucleic acid cargo may be circular, e.g. a minicircle or plasmid. The nucleic acid cargo may be linear. The nucleic acid cargo may be DNA or RNA.

The extracellular vesicle may be a microvesicle or an exosome.

An extracellular vesicle loaded with a nucleic acid cargo, which is prepared or obtained by a method according to the present disclosure is also provided.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which:

FIG. 1A: Unloaded RBCEVs, RBCEVs mixed with GFP mRNA (RBCEVs+mRNA), and RBCEVs with GFP mRNA loaded by electroporation (mRNA-eRBCEVs) were added to 293T cells. After 48 h, cells were imaged by microscopy and GFP-positive cells were quantified using flow cytometry. FIG. 1B: Unloaded RBCEVs, RBCEVs mixed with GFP minicircles (RBCEVs+MC), and RBCEVs with GFP minicircles loaded by electroporation (MC-eRBCEVs) were added to 293T cells. After 48 h, cells were imaged by microscopy and GFP-positive cells were quantified using flow cytometry.

FIG. 3A: RBCEVs or MSC-exo were chemically transfected with minicircle DNA encoding GFP and thereafter treated to 293T cells (MC-RBCEVs and MC-MSC-exo). Minicircle DNA in the absence of EVs was used as a control (MC Control). After 48 h, cells were imaged by microscopy and GFP-positive cells were quantified using flow cytometry. FIG. 3B: Percentage of GFP-positive cells in each group. n=3, *p<0.001 (Student's t-test)

FIG. 7A: DNA constructs of increasing sizes (Lanes 1-2.kb; 2-6.6 kb, 3-9.6 kb, 4-11.4 kb; 5-34.2 kb) were linearized through restriction digestion of a single unique cut site and separated by agarose gel electrophoresis. These constructs each contain a single copy of the copGFP transgene driven by a CMV promoter. FIG. 7B: RBCEVs were loaded with each of these constructs and were added to HEK293T cells. 48 h after transgene expression was detected using fluorescence microscopy. FIG. 7C: Transgene expressing cells were also analysed by flow cytometry. Representative dot plot for each DNA cargo is depicted with percentage of GFP-positive cells indicated in the gated region. Mean fluorescence intensities are plotted in a bar chart (n=3).

FIG. 9A: 6-week old female NSG mice were administered with unloaded RBCEVs (n=3) or luciferase-encoding MC-loaded RBCEVs (n=3) via tail vein injection on Day 0. Line graph depicts luciferase activity tracked over time by whole body bioluminescence imaging following the injection of luciferin substrate, at timepoints indicated by the x-axis. Representative ventral and dorsal images of the mice at the indicated timepoints are shown on the left. FIG. 9B: In vivo delivery of DNA plasmids of sizes up to 34 kb. 6-week old female BALB/c mice were administered with unloaded RBCEVs (n=2) or RBCEVs loaded with luciferase-encoding 2 kb, 8 kb and 34 kb DNA cargoes (n=2) via tail vein injection on Day 0. Luciferase activity was assessed after 48 h by whole body bioluminescence imaging following the injection of luciferin substrate. Whole-body luminescence images of the mice are shown on the left. Average bioluminescent photon flux of the mice treated with different sized DNA cargoes are shown on the right.

DETAILED DESCRIPTION OF THE INVENTION

Figure 1A:
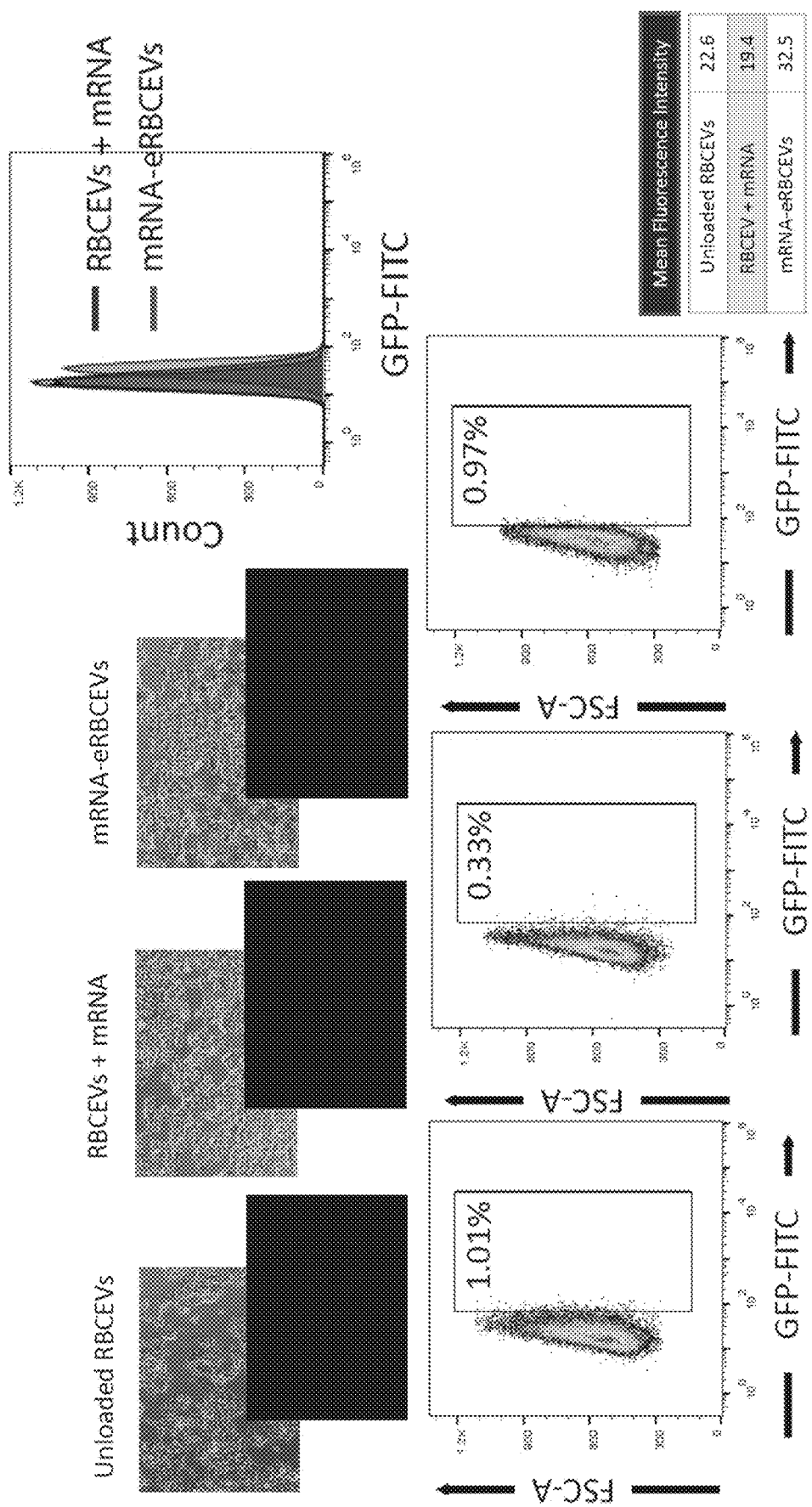
FIGS. 1A-1B. Delivery of mRNA vs DNA into 293T cells by electroporated RBCEVs.

Aspects and embodiments of the present invention will now be discussed with reference to the accompanying figures. Further aspects and embodiments will be apparent to those skilled in the art. All documents mentioned in this text are incorporated herein by reference.

Extracellular Vesicles

The term "extracellular vesicle" (EV) as used herein refers to a small vesicle-Ike structure released from a cell into the extracellular environment. In particularly preferred aspects disclosed herein, the extracellular vesicles are derived from red blood cells (RBCEVs).

Extracellular vesicles (EVs) are substantially spherical fragments of plasma membrane or endosomal membrane between 50 and 1000 nm in diameter. Extracellular vesicles are released from various cell types under both pathological and physiological conditions. Extracellular vesicles have a membrane. The membrane may be a double layer membrane (i.e. a lipid bilayer). The membrane may originate from the plasma membrane. Accordingly, the membrane of the extracellular vesicle may have a similar composition to the cell from which it is derived. In some aspects disclosed herein, the extracellular vesicles are substantially transparent.

The term extracellular vesicles encompasses exosomes, microvesicles, membrane microparticles, ectosomes, blebs and apoptotic bodies. Extracellular vesicles may be produced via outward budding and fission. The production may be a natural process, or a chemically induced or enhanced process. In some aspects disclosed herein, the extracellular vesicle is a microvesicle produced via chemical induction.

Extracellular vesicles may be classified as exosomes, microvesicles or apoptotic bodies, based on their size and origin of formation. Microvesicles are a particularly preferred class of extracellular vesicle according to the invention disclosed herein. Preferably, the extracellular vesicles of the invention have been shed from the plasma membrane, and do not originate from the endosomal system. In certain aspects described herein, the extracellular vesicles are not exosomes. In preferred aspects described herein, the extracellular vesicles are red blood cell derived extracellular vesicles, derived from the plasma membrane of a red blood cell through outward budding and fission of the plasma membrane.

In some aspects and embodiments of the present disclosure the extracellular vesicle is not an exosome. In some aspects and embodiments of the present disclosure the extracellular vesicle is not an ectosome. In some aspects and embodiments of the present disclosure the extracellular vesicle is not a bleb. In some aspects and embodiments of the present disclosure the extracellular vesicle is not an apoptotic body.

In some aspects and embodiments of the present disclosure the extracellular vesicle is a microvesicle or a membrane microparticle.

Extracellular vesicles disclosed herein may be derived from various cells, such as red blood cells, white blood cells, cancer cells, stem cells, dendritic cells, macrophages and the like. In a preferred embodiment, the extracellular vesicles are derived from a red blood cell, although extracellular vesicles from any source may be used, such as from leukemia cells and cell lines. In preferred aspects described herein, the extracellular vesicles are derived from red blood cells.

Microvesicles or microparticles arise through direct outward budding and fission of the plasma membrane. Microvesicles are typically larger than exosomes, having diameters ranging from 100-500 nm. In some cases, a composition of microvesicles comprises microvesicles with diameters ranging from 50-1000 nm, from 50-750 nm, from 50-500 nm, from 50-300 nm, from 50-200 nm, from 50-150 nm, from 101-1000 nm, from 101-750 nm, from 101-500 nm, from 101-300 nm, from 100-300 nm, or from 100-200 nm. Preferably, the diameters are from 100-300 nm.

A population of microvesicles, for example as present in a composition, pharmaceutical composition, medicament or preparation, will comprise microvesicles with a range of different diameters, the median diameter of microvesicles within a microvesicle sample can range 50-1000 nm, from 50-750 nm, from 50-500 nm, from 50-300 nm, from 50-200 nm, from 50-150 nm, from 101-1000 nm, from 101-750 nm, from 101-500 nm, from 101-300 nm, from 100-300 nm, from 100-200 nm, or from 100-150 nm. Preferably, the median diameter is in one of the ranges: 50-300 nm, 50-200 nm, 50-150 nm, 100-300 nm, 100-200 nm, or 100-150 nm. The mean average diameter may be one of 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, optionally ±1, 2, 3, 4, 5, 6, 7, 8, 9 or 10 nm.

The diameter of exosomes ranges from around 30 to around 100 nm. In some cases, a population of exosomes, as may be present in a composition, comprises exosomes with diameters ranging from 10-200 nm, from 10-150 nm, from 10-120 nm, from 10-100 nm, from 20-150 nm, from 20-120 nm, from 25-110 nm, from 25-100 nm, or from 30-100 nm. Preferably, the diameters are from 30-100 nm. A population of exosomes, for example as present in a composition, pharmaceutical composition, medicament or preparation, will comprise exosomes with a range of different diameters, the median diameter of exosomes within a sample can range ranging from 10-200 nm, from 10-150 nm, from 10-120 nm, from 10-100 nm, from 20-150 nm, from 20-120 nm, from 25-110 nm, from 25-100 nm, or from 30-100 nm. Preferably, the median diameter is between 30-100 nm. The mean average diameter may be one of 10 nm, 20 nm, 30 nm, 40 nm, 50 nm, 60 nm, 70 nm, 80 nm, 90 nm, 100 nm, 110 nm, or 120 nm, optionally ±1, 2, 3, 4, 5, 6, 7, 8, 9 or 10 nm.

A population of extracellular vesicles may comprise one of at least 10, 100, 1000, $10^4$, $10^5$, $10^6$, $10^7$, $10^8$, $10^9$, $10^{10}$, $10^{11}$, $10^{12}$, $10^{13}$ or $10^{14}$ extracellular vesicles (optionally per ml of carrier).

Exosomes are observed in a variety of cultured cells including lymphocytes, dendritic cells, cytotoxic T cells, mast cells, neurons, oligodendrocytes, Schwann cells, and intestinal epithelial cells. Exosomes originate from the endosomal network that locates in within multivesicular bodies, large sacs in the cytoplasm. These sacs fuse to the plasma membrane, before being released into extracellular environment.

Apoptotic bodies or blebs are the largest extracellular vesicles, ranging from 1-5 μm. Nucleated cells undergoing apoptosis pass through several stages, beginning with condensation of the nuclear chromatin, membrane blebbing and finally release of EVs including apoptotic bodies.

Preferably, the extracellular vesicles are derived from human cells, or cells of human origin. The extracellular vesicles of the invention may have been induced from cells contacted with a vesicle inducing agent. The vesicle inducing agent may be calcium ionophore, lysophosphatidic acid (LPA), or phorbol-12-myristat-13-acetate (PMA). Preferably, the vesicle inducing agent is calcium ionophore.

In many aspects described herein, the cells are not modified. In particular, the cells from which the extracellular vesicles are derived do not comprise exogenous nucleic acid or proteins. In some cases, the cells are ex vivo, such as resulting from a blood draw. In some cases, the cells have not been modified, such as transduced, transfected, infected, or otherwise modified, but are substantially unchanged as compared to the cells in vivo. Where the cells are red blood cells, the cells may contain no DNA, or may contain substantially no DNA. The red blood cells may be DNA free. Accordingly, in preferred embodiments the extracellular vesicles are loaded with their nucleic acid cargo after the extracellular vesicles have been formed and isolated. Preferably, the extracellular vesicles do not contain nucleic acid, particularly DNA, that was present in the cells from which they are derived. For example, it is preferred that the extracellular vesicles do not contain genomic or mitochondrial DNA.

Red Blood Cell Extracellular Vesicles (RBCEVs)

In certain aspects disclosed herein, the extracellular vesicles are derived from red blood cells (erythrocytes). Red blood cells are a good source of EVs for a number of reasons. Because red blood cells are enucleated, RBCEVs contain less nucleic acid than EVs from other sources. RBCEVs do not contain endogenous DNA. RBCEVs may contain miRNA or other RNAs. RBCEVs are free from oncogenic substances such as oncogenic DNA or DNA mutations. Because red blood cells lack organelles (including endosomes), RBCEVs cannot be derived from endosomes, and thus are not exosomes. Instead, RBCEVs are derived from outward budding of the plasma membrane of the red blood cell. As such, the membrane of RBCEVs has a composition that is very similar to that of a red blood cell, such as having a bending modulus of around 15 $k_BT$, such as between 14 and 16 $k_BT$, between 13 and 17 $k_BT$, between 12 and 18 $k_BT$ which is similar to the bending modulus found in studies of the membrane of red blood cells. Bending modulus may be assessed using the vesicle stiffness, radius and thether force, as set out in Daan Vorselen et al. (2018) Nature Communications 9: 4960.

A method for isolation and characterisation of RBCEVs is described in Usman et al. (Efficient RNA drug delivery using red blood cell extracellular vesicles. Nature Communications 9, 2359 (2018) doi:10.1038/s41467-018-04791-8), incorporated herein in its entirety by reference.

RBCEVs may comprise haemoglobin and/or stomatin and/or flotillin-2. They may be red in colour. Typically RBCEVs exhibit a domed (concave) surface, or "cup shape" under transmission electron microscopes. The RBCEV may be characterised by having cell surface CD235a. RBCEVs may comprise red blood cell markers such as haemoglobin a or stomatin.

RBCEVs according to the invention may be about 100 nm to about 300 nm in diameter. In some cases, a composition of RBCEVs comprises RBCEVs with diameters ranging from 50-1000 nm, from 50-750 nm, from 50-500 nm, from 50-300 nm, from 50-200 nm, from 50-150 nm, from 101-1000 nm, from 101-750 nm, from 101-500 nm, from 101-300 nm, from 100-300 nm, from 100-200 nm or from 100-150 nm. Preferably, the diameters are from 50-300 nm, from 50-200 nm, from 50-150 nm, 100-300 nm, from 100-200 nm, or from 100-150 nm.

A population of RBCEVs, e.g. as may be present in a composition, will comprise RBCEVs with a range of different diameters, the median diameter of RBCEVs within a RBCEV sample can range from 50-1000 nm, from 50-750 nm, from 50-500 nm, from 50-300 nm, from 50-200 nm, from 50-150 nm, from 101-1000 nm, from 101-750 nm, from 101-500 nm, from 101-300 nm, from 100-300 nm, from 100-200 nm or from 100-150 nm. Preferably, the median diameter is between 50-300 nm, from 50-200 nm, from 50-150 nm, 100-300 nm, from 100-200 nm, or from 100-150 nm. The mean average diameter may be one of 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, optionally ±1, 2, 3, 4, 5, 6, 7, 8, 9 or 10 nm.

Preferably, the RBCEVs are derived from a human or animal blood sample or red blood cells derived from primary cells or immobilized red blood cell lines. The blood cells may be type matched to the patient to be treated, and thus the blood cells may be Group A, Group B, Group AB, Group O or Blood Group Oh. Preferably the blood is Group O. The blood may be rhesus positive or rhesus negative. In some cases, the blood is Group O and/or rhesus negative, such as Type O−. The blood may have been determined to be free from disease or disorder, such as free from HIV, sickle cell anaemia, malaria. However, any blood type may be used. In some cases, the RBCEVs are autologous and derived from a blood sample obtained from the patient to be treated. In some cases, the RBCEVs are allogenic and not derived from a blood sample obtained from the patient to be treated.

RBCEVs may be isolated from a sample of red blood cells. Protocols for obtaining EVs from red blood cells are known in the art, for example in Danesh et al. (2014) Blood. 2014 Jan. 30; 123(5): 687-696. Methods useful for obtaining EVs may include the step of providing or obtaining a sample comprising red blood cells, inducing the red blood cells to produce extracellular vesicles, and isolating the extracellular vesicles. The sample may be a whole blood sample. Preferably, cells other than red blood cells have been removed from the sample, such that the cellular component of the sample is red blood cells.

The red blood cells in the sample may be concentrated, or partitioned from other components of a whole blood sample, such as white blood cells. Red blood cells may be concentrated by centrifugation. The sample may be subjected to leukocyte reduction.

The sample comprising red blood cells may comprise substantially only red blood cells. Extracellular vesicles may be induced from the red blood cells by contacting the red blood cells with a vesicle inducing agent. The vesicle inducing agent may be calcium ionophore, lysophosphatidic acid (LPA), or phorbol-12-myristat-13-acetate (PMA).

RBCEVs may be isolated by centrifugation (with or without ultracentrifugation), precipitation, filtration processes such as tangential flow filtration, or size exclusion chromatography (e.g. see Usman et al., supra). In this way, RBCEVs may be separated from RBCs and other components of the mixture.

Extracellular vesicles may be obtained from red blood cells by a method comprising: obtaining a sample of red blood cells; contacting the red blood cells with a vesicle inducing agent; and isolating the induced extracellular vesicles.

The red blood cells may be separated from a whole blood sample containing white blood cells and plasma by low speed centrifugation and using leukodepletion filters. In some cases, the red blood cell sample contains no other cell types, such as white blood cells. In other words, the red blood cell sample consists substantially of red blood cells. The red blood cells may be diluted in buffer such as PBS prior to contacting with the vesicle inducing agent. The vesicle inducing agent may be calcium ionophore, lysophosphatidic acid (LPA) or phorbol-12-myristat-13-acetate (PMA). The vesicle inducing agent may be about 10 nM calcium ionophore. The red blood cells may be contacted with the vesicle inducing agent overnight, or for at least 1, at least 2, at least 3, at least 4, at least 5, at least 6, at least 7, at least 8, at least 9, at least 10, at least 11, at least 12 or more than 12 hours. The mixture may be subjected to low speed centrifugation to remove RBCs, cell debris, or other non-RBCEVs matter and/or passing the supernatant through an about 0.45 μm syringe filter. RBCEVs may be concentrated by ultracentrifugation, such as centrifugation at around 100,000×g. The RBCEVs may be concentrated by ultracentrifugation for at least 10 minutes, at least 20 minutes, at least 30 minutes, at least 40 minutes, at least 50 minutes or at least one hour. The concentrated RBCEVs may be suspended in cold PBS. They may be layered on a 60% sucrose cushion. The sucrose cushion may comprise frozen 60% sucrose. The RBCEVs layered on the sucrose cushion may be subject to ultracentrifugation at 100,000 g for at least one hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours or more. Preferably, the RBCEVs layered on the sucrose cushion may be subject to ultracentrifugation at 100,000 g for about 16 hours. The red layer above the sucrose cushion is then collected, thereby obtaining RBCEVs. The obtained RBCEVs may be subject to further processing, such as washing, tagging, and optionally loading.

Surface Tagging

Extracellular vesicles within the composition may comprise a tag, preferably attached to, or inserted through, the vesicle membrane.

The extracellular vesicles may have, at their surface, a tag. The tag is preferably a protein or peptide sequence. The tag may be a peptide or protein. It may be a modified peptide or protein, such as a glycosylated or biotinylated protein or peptide. The tag may be covalently linked to the extracellular vesicle, such as covalently linked to a membrane protein in the extracellular vesicle. The tag may have been added to the extracellular vesicle after the extracellular vesicle had formed. The tag may be linked to the extracellular vesicle by a sequence that comprises or consists of a sequence that is, or that is derived from, a protein ligase recognition sequence. For example, the tag may be linked to the extracellular vesicle by a sequence that comprises 100% sequence identity to a protein ligase recognition sequence, or about 90%, about 80%, about 70%, about 60%, about 50% or about 40% sequence identity to a protein ligase recognition sequence. The amino acid sequence may comprises LPXT.

The tag may be presented on the external surface of the vesicle, and is thus exposed to the extravesicular environment.

The tag may be an exogenous molecule. In other words, the tag is a molecule that is not present on the external surface of the vesicle in nature. In some cases, the tag is an exogenous molecule that is not present in the cell or red blood cell from which the extracellular vesicle is derived.

The tag may increase the stability, uptake efficiency and availability in the circulation of the extracellular vesicles.

In some cases, the tag acts to present the extracellular vesicles and extracellular vesicles containing cargoes in the circulation and organs in the body. The peptides and proteins can act as therapeutic molecules such as blocking/activating target cell function or presenting antigens for vaccination. They can also act as probes for biomarker detection such as diagnosis of toxins.

The tag may contain a functional domain and a protein ligase recognition sequence. The functional domain may be capable of binding to a target moiety, capable of detection, or capable of inducing a therapeutic effect. The functional domain may be capable of binding to a target molecule. Tags comprising such a functional domain may be referred to herein as binding molecules. A binding molecule is one that is capable of interacting specifically with a target molecule. Extracellular vesicles comprising a binding moiety may be particularly useful for delivering a cargo or a therapeutic agent to a cell that has the target molecule. Suitable binding molecules include antibodies and antigen binding fragments (sometimes known as antibody fragments), ligand molecules and receptor molecules. The binding molecule will bind to a target of interest. The target may be a molecule associated with, such as expressed on the surface of, a cell of interest. The ligand may form a complex with a biomolecule on the target cell, such as a receptor molecule.

Suitable binding molecules include antibodies and antigen binding fragments. Fragments, such as Fab and Fab2 fragments may be used as can genetically engineered antibodies and antibody fragments. The variable heavy (VH) and variable light (VL) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855). Antibodies or antigen binding fragments useful in the extracellular vesicles disclosed herein will recognise and/or bind to, a target molecule.

That antigenic specificity is conferred by variable domains and is independent of the constant domains is known from experiments involving the bacterial expression of antibody fragments, all containing one or more variable domains. These molecules include Fab-like molecules (Better et al. (1988) Science 240, 1041); Fv molecules (Skerra et al. (1988) Science 240, 1038); single-chain Fv (ScFv) molecules where the VH and VL partner domains are linked via a flexible oligopeptide (Bird et al. (1988) Science 242, 423; Huston et al. (1988) Proc. Natl. Acad. Sd. USA 85, 5879) and single domain antibodies (dAbs) comprising isolated V domains (Ward et al. (1989) Nature 341, 544). A general review of the techniques involved in the synthesis of antibody fragments which retain their specific binding sites is to be found in Winter & Milstein (1991) Nature 349, 293-299. Antibodies and fragments useful herein may be human or humanized, murine, camelid, chimeric, or from any other suitable source.

By "ScFv molecules" we mean molecules wherein the VH and VL partner domains are covalently linked, e.g. directly, by a peptide or by a flexible oligopeptide. Fab, Fv, ScFv and sdAb antibody fragments can all be expressed in and secreted from *E. coli*, thus allowing the facile production of large amounts of the said fragments.

Whole antibodies, and F(ab')2 fragments are "bivalent". By "bivalent" we mean that the said antibodies and F(ab')2 fragments have two antigen combining sites. In contrast, Fab, Fv, ScFv and sdAb fragments are monovalent, having only one antigen combining site. Monovalent antibody fragments are particularly useful as tags, because of their small size.

A preferred binding molecule may be a sdAb. By "sdAb" we mean single domain antibody consisting of one, two or more single monomeric variable antibody domains. sdAb molecules are sometimes referred to as dAb.

In some cases, the binding molecule is a single chain antibody, or scAb. A scAb consists of covalently linked VH and VL partner domains (e.g. directly, by a peptide, or by a flexible oligopeptide) and optionally a light chain constant domain.

Other suitable binding molecules include ligands and receptors that have affinity for a target molecule. The tag may be a ligand of a cell surface receptor. Examples include streptavidin and biotin, avidin and biotin, or ligands of other receptors, such as fibronectin and integrin. The small size of biotin results in little to no effect to the biological activity of bound molecules. As biotin and streptavidin, biotin and avidin, and fibronectin and integrin bind their pairs with high affinity and specificity, they are very useful as binding molecules. The Avidin-biotin complex is the strongest known non-covalent interaction (Kd=10-15M) between a protein and ligand. Bond formation is rapid, and once formed, is unaffected by extremes of pH, temperature, organic solvents and other denaturing agents. The binding of biotin to streptavidin and is also strong, rapid to form and useful in biotechnology applications.

The functional domain may comprise or consist of a therapeutic agent. The therapeutic agent may be an enzyme. It may be an apoptotic inducer or inhibitor.

The functional domain may comprise an antigen or antibody recognition sequence. The tag may comprise one or more short peptides derived from one or more antigenic peptides. The peptide may be a fragment of an antigenic peptide. Suitable antigenic peptides are known to one of skill in the art.

The functional domain may comprise or consist of a detectable moiety. Detectable moieties include fluorescent labels, colorimetric labels, photochromic compounds, magnetic particles or other chemical labels. The detectable moiety may be biotin or a His tag.

The tag may comprise a spacer or linker moiety. The spacer or linker may be arranged between the tag and the protein ligase recognition sequence. The spacer or linker may be linked to the N or C terminus of the tag. The spacer or linker may be arranged so as not to interfere or impede the function of the tag, such as the target binding activity by the tag. The spacer or linker may be a peptide sequence. In some case, the spacer or linker is a series of at least 1, at least 2, at least 3, at least 4, at least 5, at least 6, at least 7, at least 8, at least 9, at least 10 amino acids, at least 11 amino acids, at least 12 amino acids, at least 13 amino acids, at least 14 amino acids or at least 15 amino acids. The spacer or linker may be flexible. The spacer may comprise a plurality of glycine and/or serine amino acids.

Spacer and linker sequences are known to the skilled person, and are described, for example in Chen et al., Adv Drug Deliv Rev (2013) 65(10):1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10):1357-1369. Flexible linker sequences often comprise high proportions of glycine and/or serine residues.

In some cases, the spacer or linker sequence comprises at least one glycine residue and/or at least one serine residue. In some embodiments the linker sequence consists of glycine and serine residues. In some cases, the spacer or linker sequence has a length of 1-2, 1-3, 1-4, 1-5 or 1-10 amino acids.

Inclusion of the spacer or linker may improve the efficiency of the protein ligase reaction between the extracellular vesicle and the tag moiety. The term "tag" as used herein may encompass a peptide comprising a tag, a spacer, and protein ligase recognition sequence.

Suitable protein ligase recognition sequences are known in the art. The protein ligase recognition sequence is recognised by the protein ligase used in the method of tagging the extracellular vesicles. For example, if the protein ligase used in the method is a sortase, then the protein ligase recognition sequence is a sortase binding site. In those cases, the sequence may be LPXTG (where X is any naturally occurring amino acid), preferably LPETG. Alternatively, where the enzyme is AEP1, the protein ligase recognition sequence may be NGL. The protein ligase binding site may be arranged at the C terminus of the peptide or protein.

The tag may additionally comprise one or more further sequences to aid in purification or processing of the tag, during production of the tag itself, during the tagging method, or for subsequent purification. Any suitable sequence known in the art may be used. For example, the sequence may be an HA tag, a FLAG tag, a Myc tag, a His tag (such as a poly His tag, or a 6×His tag).

The tag may be linked to substantially all of the extracellular vesicles in a population or composition. Compositions disclosed herein may comprise extracellular vesicles in which at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, or at least 97% of the extracellular vesicles comprise the tag. Preferably, at least 85%, at least 90%, at least 95%, at least 96% or at least 97% of the extracellular vesicles comprise the tag. In some cases, different extracellular vesicles within the composition comprise different tags. In some cases, the extracellular vesicles comprise the same, or substantially the same, tag.

Methods for incorporating a tag are described in PCT/SG2019/050481, WO 2014/183071 A2, WO 2014/83066 A2 and US 2014/0030697 A1, each incorporated herein by reference in its entirety.

Cargo

Extracellular vesicles disclosed herein may be loaded with, or contain, a cargo. The present disclosure is particularly concerned with nucleic acid cargo which comprises, or consists of, DNA (deoxyribonucleic acid), RNA (ribonucleic acid) or a chemically modified DNA or RNA. In preferred embodiments the cargo comprises, or consists of, DNA or a chemically modified DNA. The term "cargo" is used interchangeably with "load" herein.

A nucleic acid cargo refers to a nucleic acid (e.g. oligonucleotide or polynucleotide) loaded into or onto an extracellular vesicle. A nucleic acid cargo normally refers to an oligonucleotide strand (which may be in any form, e.g. single stranded, double stranded, super-coiled or not super-coiled, chromosomal or non-chromosomal). The DNA may be conjugated to, or complexed with, other molecules, e.g. carriers, stabilisers, histones, lipophilic agents.

Methods disclosed herein may be used for any nucleic acid cargo, but are particularly advantageous for loading large nucleic acids, and particularly for loading DNA cargo. Nucleic acid may be double or single stranded. Preferably, the nucleic acid is double stranded. The nucleic acid may be circular.

The cargo is preferably exogenous. In other words, the nucleic acid is not present in the extracellular vesicles when they are newly generated, and/or in the cells from which the extracellular vesicles are derived. The cargo may be synthetic, having been designed and/or constructed in vitro or in silico.

The cargo may be a therapeutic oligonucleotide or a diagnostic oligonucleotide. The nucleic acid may encode a gene of interest. For example, the cargo may encode a functional gene to replace an absent gene, repair a defective gene, or induce a therapeutic effect in a target tissue. In some cases, the cargo is a reporter gene or encodes a molecule that is readily detectable.

The cargo may comprise an expression vector or expression cassette sequence. Suitable expression vectors and expression cassettes are known art. Expression vectors useful in the methods described herein comprise elements that facilitate the expression of one or more nucleic acid sequences in a target cell. Expression vectors useful in the present disclosure may comprise a transgene or other DNA sequence.

An expression vector refers to an oligonucleotide molecule (e.g. DNA or RNA) used as a vehicle to transfer foreign genetic material into a cell for expression in/by that cell. Such vectors may include a promoter sequence operably linked to the nucleotide sequence encoding the gene sequence to be expressed. A vector may also include a termination codon and expression enhancers. Any suitable promoters, enhancers and termination codons known in the art may be used.

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein, peptide or polypeptide. Desired proteins, peptides and polypeptides include full-length antibodies and antibody fragments, hormones, cytokines, enzymes, peptide antibiotics, protein prodrugs, marker proteins, membrane proteins, transporter proteins, receptor proteins, growth factors, histones, chaperones, structural proteins, transcription factors, signaling proteins, nucleic acid-binding proteins, lipid-binding proteins, membrane fusion proteins, cell adhesion proteins and clotting factors.

Examples of circular cargo molecules include minicircles and plasmids.

The nucleic acid cargo may be a minicircle. Minicircles are small (around 4 kbp) circular replicons. Minicircles usually comprise DNA, normally double stranded. Although minicircles occur naturally in some eukaryotic organelle genomes, minicircles preferred herein are synthetically derived. In some cases, the minicircle does not comprise an origin of replication, and thus does not replicate within the cell. Minicircles disclosed herein may be about 1.5 kbp, about 2 kbp, about 2.5 kbp, about 3 kbp, about 3.5 kbp, about 4 kbp, about 4.5 kbp, about 5 kbp, about 5.5 kbp, about 6 kbp, about 6.5 kbp or about 7 kbp. Minicircles are known to those of ordinary skill in the art, e.g. see Gaspar et al., Minicircle DNA vectors for gene therapy: advances and applications. Expert Opin Biol Ther 2015 March; 15(3): 353-79. doi: 10.1517/14712598.2015.996544. Epub 2014 Dec. 24.

In some cases, the nucleic acid cargo is a plasmid. A plasmid is normally able to replicate independently in a cell. Plasmids usually comprise DNA, normally double stranded, and may range in size of about 1 kbp to several megabase pairs (Mbp). The plasmid may comprise an origin of replication sequence.

In some cases, the nucleic acid is a DNA Dumbbell. DNA Dumbbells are minimal vectors comprising a linear double-stranded DNA expression cassette which is covalently closed at both ends with single-stranded loop structures. DNA Dumbbells may be synthesised by enzymatic ligation assisted by nucleases (ELAN), involving simultaneous intermolecular ligation and digestion of misligated off-pathway products. Alternatively, DNA Dumbbells may be synthesised in a two-step method in which the expression cassette is first amplified by PCR using chemically modified primers to form a ready-to-ligate DNA structure, and subsequently subject to a highly efficient intramolecular ligation reaction (e.g. Yu et al., Nucleic Acids Res. 2015 Oct. 15; 43(18): e120).

In some cases, the cargo is a nucleic acid that is, or that encodes an siRNA or antisense oligonucleotide (ASO). Such cargo may be useful in methods of gene silencing. The siRNA or ASO may correspond to a sequence that is expressed in a target cell. It may act to inhibit or enhance the expression of a particular gene or protein of interest. The nucleic acid may encode an siRNA or ASO corresponding to a miRNA expressed in a target cell.

The cargo may comprise or encode an mRNA. The mRNA may encode a transgene.

In some cases the nucleic acid is not modified to contain a sequence that binds to a protein on the surface of the vesicle. For example, the cargo nucleic acid does not contain a trans activating response (TAR) element. In some cases, the extracellular vesicle is not modified to contain a modified surface protein, such as an exogenous ARRDC1 protein or sequence derived from an ARRDC1 protein.

In some cases, the nucleic acid cargo comprises one or more modified nucleotides or other modifications. Chemical modifications may include chemical substitution at a sugar position, a phosphate position, and/or a base position of the nucleic acid including, for example, incorporation of a modified nucleotide, incorporation of a capping moiety (e.g. 3' capping), conjugation to a high molecular weight, non-immunogenic compound (e.g. polyethylene glycol (PEG)), conjugation to a lipophilic compound, substitutions in the phosphate backbone. For example, the nucleic acid may comprise one or more 2'-position sugar modifications, such as 2'-amino (2'-NH), 2'-fluoro (2'-F), and 2'-O-methyl (2'-OMe). Base modifications may include 5-position pyrimidine modifications, 8-position purine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. Nucleic acids may be of variant types, such as locked nucleic acid (LNA), or gapmer.

Extracellular vesicles according to the present disclosure may comprise (e.g. be loaded with) at least 0.1 nucleic acid molecules per vesicle. The extracellular vesicle(s) may comprise (e.g. be loaded with) one of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 or more copies of the nucleic acid per vesicle. The extracellular vesicle(s) may comprise (e.g. be loaded with) one of at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 copies of the nucleic acid per vesicle. The extracellular vesicle(s) may comprise (e.g. be loaded with) at least 0.5, at least 1, at least 2, at least 3, at least 3.5, at least 4, at least 5 or more copies per vesicle. The extracellular vesicle(s) may comprise (e.g. be loaded with) about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more copies of the nucleic acid per vesicle. The extracellular vesicle(s) may comprise (e.g. be loaded with) one of 0.1-1.0, 0.1-2.0, 0.1-3.0, 0.1-4.0, 0.1-5.0, 0.1-6.0, 0.1-7.0, 0.1-8.0, 0.1-9.0, 0.1-10, 0.1-15.0, 0.1-20.0, 0.1-25.0, 0.1-30.0, 0.1-35.0, 0.1-40.0, 0.1-45.0, 0.1-50, 1-2, 1-3, 1-4, 1-5, 1-6, 1-7, 1-8, 1-9, 1-10, 1-15, 1-20, 1-25, 1-30, 1-35, 1-40, 1-45, 1-50, 2-3, 2-4, 2-5, 2-6, 2-7, 2-8, 2-9, 2-10, 2-15, 2-20, 2-25, 2-30, 2-35, 2-40, 2-45, 2-50, 3-4, 3-5, 3-6, 3-7, 3-8, 3-9, 3-10, 3-15, 3-20, 3-25, 3-30, 3-35, 3-40, 3-45, 3-50, 4-5, 4-6, 4-7, 4-8, 4-9, 4-10, 4-15, 4-20, 4-25, 4-30, 4-35, 4-40, 4-45, 4-50, 5-6, 5-7, 5-8, 5-9, 5-10, 5-15, 5-20, 5-25, 5-30, 5-35, 5-40, 5-45, 5-50, 6-7, 6-8, 6-9, 6-10, 6-15, 6-20, 6-25, 6-30, 6-35, 6-40, 6-45, 6-50, 7-8, 7-9, 7-10, 7-15, 7-20, 7-25, 7-30, 7-35, 7-40, 7-45, 7-50, 8-9, 8-10, 8-15, 8-20, 8-25, 8-30, 8-35, 8-40, 8-45, 8-50, 9-10, 9-15, 9-20, 9-25, 9-30, 9-35, 9-40, 9-45, 9-50, 10-15, 10-20, 10-25, 10-30, 10-35, 10-40, 10-45, 10-50, 15-20, 15-25, 15-30, 15-35, 15-40, 15-45, 15-50, 20-25, 20-30, 20-35, 20-40, 20-45, 20-50, 25-30, 25-35, 25-40, 25-45, 25-50, 30-35, 30-40, 30-45, 30-50, 35-40, 35-45, 35-50, 40-45, 40-50, or 45-50 copies of the nucleic acid per vesicle.

The number of the nucleic acid(s) per vesicle may be an average number, preferably mean average, across a population of EVs, e.g. as present in a composition. The number of copies of nucleic acid per vesicle may be determined by dividing the total number of copies of the loaded nucleic acid cargo by the total number of EVs. In other words, Copies per EV=Number of loaded copies of nucleic acid/Total number of EV particles. The number of copies of nucleic acid may be determined by qPCR. The number of EVs may be determined by nanoparticle tracking analysis (NPA, e.g. as described in Wang et al., ASMMs as a versatile platform for intracellular delivery of macromolecules. Nature Communications 2018 9-960). Nanoparticle tracking analysis (NTA) is a method for visualizing and analyzing particles in liquids. The technique is used in conjunction with an ultramicroscope and a laser illumination unit that together allow small particles in liquid suspension to be visualized moving under Brownian motion. The light scattered by the particles is captured using a CCD or EMCCD camera over multiple frames. Computer software is then used to track the motion of each particle from frame to frame.

As used herein and unless indicated otherwise, the term "average" refers to the mathematical mean. This may refer to the total amount of nucleic acid determined in a sample, divided by the total number of vesicles in that sample Although it may be desirable for the cargo to be loaded into substantially all of the extracellular vesicles in a composition, compositions disclosed herein may comprise extracellular vesicles in which one of at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% of the extracellular vesicles contain the cargo. Preferably, at least one of 50%, 55%, 60%, 65%, 70%, 75%, 80%, 85%, 90%, 95%, 97%, 98%, 99%, or 100% of the extracellular vesicles contain the cargo. In some cases, different extracellular vesicles within the composition contain different cargo. In some cases, the extracellular vesicles contain the same, or substantially the same, cargo molecule.

The size of a nucleic acid cargo may be defined in terms of its length in bases (for single stranded nucleic acids) or base pairs (for double stranded nucleic acids). In this specification, where the single or double stranded nature of the nucleic acid cargo is not indicated a length given in bases (e.g. in kb (kilobases) is also a disclosure of the same length in base pairs (e.g. in kbp). As such a length of 1 kb (1000 bases) is also a disclosure of 1 kbp (1000 base pairs).

Where the nucleic acid cargo is single stranded it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750 or 11000 bases. Optionally, wherein the nucleic acid cargo is single stranded DNA (ssDNA) it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750 or 11000 bases. In preferred embodiments a single stranded nucleic acid cargo may have a minimum length of one of 2000, 2250, 2500, 2750, 3000, 3250, 3500, 3750, 4000, 4250, 4500, 4750, 5000 or more than 5000 bases.

Where the nucleic acid cargo is single stranded it may have a length of one of 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, or 7000-11000, bases.

In some embodiments where the nucleic acid cargo is single stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, or 40000 bases. The single stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, or 35000-40000 bases.

Where the nucleic acid cargo is double stranded it may have a length of one of at least 250, 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750 or 11000 base pairs. Optionally, where the nucleic acid cargo is double stranded it may have a maximum length of one of 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, 10000, 10250, 10500, 10750 or 11000 base pairs. In preferred embodiments a double stranded nucleic acid cargo may have a minimum length of one of 2000, 2250, 2500, 2750, 3000, 3250, 3500, 3750, 4000, 4250, 4500, 4750, 5000 or more than 5000 base pairs.

Where the nucleic acid cargo is double stranded it may have a length of one of 250-750, 500-1000, 1000-1500, 1500-2000, 2000-2500, 2500-3000, 3000-3500, 3500-4000, 4000-4500, 4500-5000, 5000-5500, 5500-6000, 1000-2000, 2000-3000, 3000-4000, 4000-5000, 5000-6000, 6000-7000, 7000-8000, 8000-9000, 9000-10000, 10000-11000, 250-1000, 1000-3000, 1000-4000, 1000-5000, 1000-6000, 1000-7000, 1000-8000, 1000-9000, 1000-10000, 1000-11000, 2000-4000, 2000-5000, 2000-6000, 2000-7000, 2000-8000, 2000-9000, 2000-10000, 2000-11000, 3000-5000, 3000-6000, 3000-7000, 3000-8000, 3000-9000, 3000-10000, 3000-11000, 4000-6000, 4000-7000, 4000-8000, 4000-9000, 4000-10000, 4000-11000, 5000-7000, 5000-8000, 5000-9000, 5000-10000, 5000-11000, 6000-8000, 6000-9000, 6000-10000, 6000-11000, 7000-9000, 7000-10000, or 7000-11000, base pairs.

In some embodiments where the nucleic acid cargo is double stranded it may have a length of up to one of 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, or 40000 base pairs. The double stranded nucleic acid cargo may have a length of one of 5000-10000, 5000-15000, 5000-20000, 5000-25000, 5000-30000, 5000-35000, 5000-40000, 10000-15000, 10000-20000, 10000-25000, 10000-30000, 10000-35000, 10000-40000, 15000-20000, 15000-25000, 15000-30000, 15000-35000, 15000-40000, 20000-25000, 20000-30000, 20000-35000, 20000-40000, 25000-30000, 25000-35000, 25000-40000, 30000-35000, 30000-40000, or 35000-40000 base pairs.

Each nucleic acid cargo may be between about 0.5 kb and about 4 kb, between about 0.5 kb and about 3 kb, between about 0.5 kb and about 2.5 kb, between about 1 kb and about 3 kb, between about 1.5 kb and about 2.5 kb, or about 2 kb. Each nucleic acid cargo may be at least 0.5 kb, at least 1.0 kb, at least 1.5 kb, at least 2.0 kb, at least 2.5 kb, at least 3 kb, at least 4 kb, at least 5 kb, at least 6 kb, at least 7 kb, at least 8 kb, at least 9 kb, at least 10 kb, at least 11 kb, at least 12 kb, at least 13 kb, at least 14 kb, at least 15 kb, at least 16 kb, at least 17 kb, at least 18 kb, at least 19 kb, at least 20 kb, at least 21 kb, at least 22 kb, at least 23 kb, at least 24 kb, at least 25 kb, at least 26 kb, at least 27 kb, at least 28 kb, at least 29 kb, at least 30 kb, at least 31 kb, at least 32 kb, at least 33 kb, at least 34 kb, at least 35 kb, at least 36 kb, at least 37 kb, at least 38 kb, at least 39 kb, at least 40 kb, at least 41 kb, at least 42 kb, at least 43 kb, at least 44 kb, at least 45 kb, at least 46 kb, at least 47 kb, at least 48 kb, at least 49 kb, at least 50 kb or more. In some preferred embodiments each nucleic acid cargo is at least 2 kb.

In some cases, the total nucleic acid cargo may be may be between about 0.5 kb and about 4 kb, between about 0.5 kb and about 3 kb, between about 0.5 kb and about 2.5 kb, between about 1 kb and about 3 kb, between about 1.5 kb and about 2.5 kb, or about 2 kb. Each nucleic acid cargo may be at least 0.5 kb, at least 1.0 kb, at least 1.5 kb, at least 2.0 kb, at least 2.5 kb, at least 3 kb, at least 4 kb, at least 5 kb, at least 6 kb, at least 7 kb, at least 8 kb, at least 9 kb, at least 10 kb, at least 11 kb, at least 12 kb or more. In other words, that the cargo comprises multiple nucleic acids, and the combined length of these nucleic acids in each vesicle is, on average, between about 0.5 kb and about 4 kb, between about 0.5 kb and about 3 kb, between about 0.5 kb and about 2.5 kb, between about 1 kb and about 3 kb, between about 1.5 kb and about 2.5 kb, or about 2 kb. Each nucleic acid cargo may be at least 0.5 kb, at least 1.0 kb, at least 1.5 kb, at least 2.0 kb, at least 2.5 kb, at least 3 kb, at least 4 kb, at least 5 kb, at least 6 kb, at least 7 kb, at least 8 kb, at least 9 kb, at least 10 kb, at least 11 kb, at least 12 kb, at least 13 kb, at least 14 kb, at least 15 kb, at least 16 kb, at least 17 kb, at least 18 kb, at least 19 kb, at least 20 kb, at least 21 kb, at least 22 kb, at least 23 kb, at least 24 kb, at least 25 kb, at least 26 kb, at least 27 kb, at least 28 kb, at least 29 kb, at least 30 kb, at least 31 kb, at least 32 kb, at least 33 kb, at least 34 kb, at least 35 kb, at least 36 kb, at least 37 kb, at least 38 kb, at least 39 kb, at least 40 kb, at least 41 kb, at least 42 kb, at least 43 kb, at least 44 kb, at least 45 kb, at least 46 kb, at least 47 kb, at least 48 kb, at least 49 kb, at least 50 kb or more.

In some cases, the nucleic acid cargo are homogeneous (i.e. each nucleic acid in a composition of EVs is similar or substantially identical). In some cases, the nucleic acid cargo are heterogeneous (i.e. the nucleic acid in a composition of EVs are not similar or substantially identical to each other).

In this specification, loading of an extracellular vesicle with a cargo refers to associating the extracellular vesicle and cargo in stable or semi-stable form such that the extracellular vesicle is useful as a carrier of the cargo, e.g. allowing its delivery to cells. Cargo molecules may be loaded in at least two ways. One is for the cargo to be present in the lumen of the extracellular vesicle (lumenal loading). Another is for the cargo to be attached to, adhered to, inserted through, or complexed with the external surface, e.g. membrane, of the extracellular vesicle (external surface loading). Cargo molecules loaded onto the external surface of the extracellular vesicle may usually be removed by contacting the vesicle with a nuclease, e.g. a DNase or RNase.

The inventors have shown that extracellular vesicles may be loaded by a combination of lumenal and external surface loading, and such extracellular vesicles may effectively deliver cargo nucleic acids to target cells both in vitro and in vivo.

Optionally, in some embodiments, reference to loading may be only to lumenal loading. Optionally, in some other embodiments, reference to loading may be only to external surface loading.

As described herein, loading of nucleic acid into extracellular vesicles may provide confer resistance from nucleic acid degradation in vivo or in vitro. For example, nucleic acid loaded extracellular vesicles may have increased resistance to serum degradation as compared nucleic acid not loaded into extracellular vesicles. For example, nucleic acid loaded extracellular vesicles may resist serum degradation, and thus retain nucleic acid, preferably functional nucleic acid, for at least 30 minutes, at least one hour, at least two hours, at least three hours, at least four hours, at least five hours, or more than five hours of contact with serum. Preferably, nucleic acid may still be detected after two hours of contact of the nucleic acid loaded extracellular vesicles with serum.

Method of Loading Extracellular Vesicles

Disclosed herein is an approach to loading extracellular vesicles. The approach uses chemical transduction in which extracellular vesicle(s), nucleic acid and transfection reagent are brought together under suitable conditions and for sufficient time to allow loading to occur.

Preferably, the method does not involve electroporation. Preferably, the method does not involve nanoporation.

Methods disclosed herein involve a step of contacting a nucleic acid to be loaded with a transfection reagent. Suitable transfection reagents include cationic reagents such as cationic lipid reagents. Several transfection reagents are known in the art, including Lipofectamine™ 3000™ (ThermoFisher), Turbofect™ (ThermoFisher), Lipofectamine™ MessengerMAX™ (ThermoFisher), Exofect™ (System Biosciences), and Linear Polyethylenimine Hydrochlorides, e.g. having an average molecular weight of 25,000 Da or 40,000 Da, such as PEIMax™ (Polysciences, Inc.) and jetPEI® (Polyplus transfection).

Some methods disclosed herein involve a step of preparing the nucleic acid to be loaded. In the preparing step, the nucleic acid that is to be loaded into to the extracellular vesicle is contacted with the transfection reagent under conditions suitable for the formation of a complex between the transfection reagent and the nucleic acid. The nucleic acid and the transfection reagent are contacted for sufficient time for complex formation to occur. Preferably, the nucleic acid and transfection reagent form a complex, such as a DNA:PEIMax complex. Preparation of the nucleic acid for loading may comprise further steps, such as concentration or dilution of the nucleic acid, or the addition of buffers or other reagents or media, such as Opti-MEM reduced serum media (Gibco). The nucleic acid and the transfection reagent may be contacted for at least 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes or more than 20 minutes.

Methods disclosed herein may involve a step of loading the extracellular vesicles with the nucleic acid:transfection reagent complexes. Prepared nucleic acid:transfection reagent complexes are contacted with the extracellular vesicle that is to be loaded. In preferred methods, the extracellular vesicles are added to prepared nucleic acid: transfection reagent complexes. In other words, contacting with the extracellular vesicle is performed subsequently to the contacting of the nucleic acid cargo to be loaded with the transfection reagent. Normally, the nucleic acid:transfection reagent complexes are contacted with a composition comprising a plurality of extracellular vesicles. The nucleic acid:transfection reagent complexes and extracellular vesicle may be incubated for sufficient time and under appropriate conditions to allow the extracellular vesicle to be loaded with one or more of the nucleic acid:transfection reagent complexes. The complexes may be internalised into the extracellular vesicle, or otherwise loaded onto the extracellular vesicle, such as onto the surface of the extracellular vesicle. Preferably, the complexes are internalised into the extracellular vesicle.

Following the loading step, the extracellular vesicles may be isolated, washed and/or concentrated. In preferred methods, a washing step follows the loading step. Following the loading step, the mixture may be washed with PBS. Preferably, washing comprises centrifuging the mixture to pellet the extracellular vesicles, resuspending the pellet in an appropriate buffer (such as PBS). The washing step may be repeated 1, 2, 3, 4, 5, 6 or more times.

The step of loading the extracellular vesicles with nucleic acid:transfection reagent complexes may be repeated. In other words, following a step of loading extracellular vesicles with nucleic acid:transfection reagent complexes, the extracellular vesicles may be optionally washed and contacted with further nucleic acid: transfection reagent complexes. In such methods, the extracellular vesicles to be loaded with nucleic acid:transfection reagent complexes may be loaded extracellular vesicles, and thus may already contain nucleic acid cargo. Alternatively, the extracellular vesicles may have been subject to a loading step, but have not been loaded with cargo, or have been loaded with a low level of cargo. Where a second or further loading step is required, the extracellular vesicles may be incubated with the further nucleic acid:transfection reagent complexes under the same or different conditions, and for the same or different time, as used in the preceding loading step. Following the second or further loading step, a further washing step may be used.

Preferably, the method involves incubating extracellular vesicles with nucleic acid:transfection reagent complexes, and does not involve incubating cells with nucleic acid:transfection reagent complexes and subsequently inducing the formation of extracellular vesicles from such cells.

In some aspects, the cargo is loaded to the extracellular vesicle. In some aspects, the cargo is loaded into the lumen of the extracellular vesicle. In some aspects, the cargo is loaded onto the extracellular vesicle, such as onto the membrane of the vesicle, or onto a protein of the membrane of the vesicle. In some aspects, some of the cargo is loaded into the lumen of the extracellular vesicle and some of the cargo is loaded onto the extracellular vesicle, such as onto the membrane of the vesicle, or onto a protein of the membrane of the vesicle.

The method may involve a step of removing nucleic acid cargo not contained within the lumen of the extracellular vesicle. Such a step may comprise contacting the loaded extracellular vesicle with DNAse. The loaded extracellular vesicle may be contacted with heparin prior to contact with DNAse, in order to dissociate nucleic acid or nucleic acid:transfection reagent complexes.

Compositions

Disclosed herein are compositions comprising extracellular vesicles. A composition may comprise a plurality of extracellular vesicles, forming a population of extracellular vesicles. Examples of compositions include pharmaceutical compositions and medicaments.

The compositions may comprise between $10^6$ to $10^{14}$ particles per ml. The compositions may comprise at least $10^5$ particles per ml, at least $10^6$ particles per ml, at least at least 107 particles per ml, at least $10^8$ particles per ml, at least $10^9$ particles per ml, at least $10^{10}$ particles per ml, at least $10^{11}$ particles per ml, at least $10^{12}$ particles per ml, at least $10^{13}$ particles per ml or at least $10^{14}$ particles per ml.

A population of extracellular vesicles in a composition will be expected to have a range of size characteristics, such as diameter. The population may exhibit a size distribution, having a median and mean average size, which may be different. Such characteristics are described above.

Every vesicle in a population is unlikely to contain the same amount of cargo. As such, a population of extracellular vesicles may be described in terms of an average number of cargo molecules per vesicle, as described above.

The composition may be a pharmaceutical composition. The composition may comprise one or more extracellular vesicle, and optionally a pharmaceutically acceptable carrier, diluent or excipient. Pharmaceutical compositions may be formulated for administration by a particular route of administration. For example, the pharmaceutical composition may be formulated for intravenous, intratumoral, intraperitoneal, intradermal, subcutaneous, intranasal or other administration route.

Compositions may comprise a buffer solution. Compositions may comprise a preservative compound. Compositions may comprise a pharmaceutically acceptable carrier.

The nucleic acid-containing compositions of the invention can be stored and administered in a sterile physiologically acceptable carrier, where the nucleic acid is dispersed in conjunction with any agents which aid in the introduction of the DNA into cells.

Various sterile solutions may be used for administration of the composition, including water, PBS, ethanol, lipids, etc. The concentration of the DNA will be sufficient to provide a therapeutic dose, which will depend on the efficiency of transport into the cells.

Compositions may be provided in frozen or lyophilised form.

Methods of Treatment and Uses of Extracellular Vesicles

Extracellular vesicles and compositions comprising extracellular vesicles as described herein may be used in therapy, e.g. in the treatment, prevention and/or amelioration of a disease or disorder. In particular, the therapy may be a method of gene therapy or gene silencing.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The subject to be treated may be any animal or human. The subject is preferably mammalian, more preferably human. The subject may be a non-human mammal, but is more preferably human. The subject may be male or female. The subject may be a patient. Therapeutic uses may be in human or animals (veterinary use).

Extracellular vesicles disclosed herein are useful in methods of treatment. In particular, the methods are useful for treating a subject suffering from a disease or disorder associated with a target gene. The target gene may be aberrantly expressed in the subject. The target gene may be upregulated or over-expressed in the subject, as compared to a healthy subject. The target gene may be downregulated, under-expressed or not expressed in the subject, as compared to a healthy subject. A functionally defective version of the target gene may be expressed in the subject, e.g. a mutant form (compared to functional wild type). The method may comprise the step of administering an effective amount of a loaded extracellular vesicle to said subject, wherein the loaded extracellular vesicle comprises a therapeutic nucleic acid cargo, such as a nucleic acid for increasing, decreasing or modulating the expression of a target gene in a target cell.

The extracellular vesicles disclosed herein are particularly useful for the treatment of a disease or disorder having a genetic basis (genetic disorder), such as caused by upregulation, over-expression, downregulation, under-expression or lack of expression of a target gene (e.g. compared to a healthy subject) or expression of a functionally defective copy or version of the target gene in the subject as compared to a healthy subject.

RBCEVs may be particularly useful for treating disorders of the CNS, lungs, liver, spleen or bone marrow. In some cases, the RBCEVs may be useful to treating disorders of the pancreas or heart. The target cell/tissue depends on the disorder to be treated.

The cargo may be a nucleic acid designed to inhibit or enhance expression of the target gene, or may be designed to perform gene editing to silence expression of, or correct the sequence of, the particular gene. The cargo may be a nucleic acid that encodes a peptide, polypeptide or protein that is underexpressed or incorrectly expressed in a target cell. For example, the nucleic acid may encode a functional peptide, polypeptide or protein that is not expressed, underexpressed, or expressed incorrectly, thereby repairing or compensating for incorrect protein function in the target cell.

Administration of the loaded EVs described herein may result in expression of protein, peptide or polypeptide encoded by the nucleic acid cargo in the patient. For example, expression of the DNA and/or transgene in the patient. Administration of the loaded EVs described herein may result in expression of protein, peptide or polypeptide in a target cell of a patient. Administration of the loaded EVs described herein may result in expression of protein, peptide or polypeptide in a cell of the CNS, lung, liver, spleen, bone marrow, pancreas or heart cell of a patient.

Extracellular vesicles and compositions described herein may be administered, or formulated for administration, by a number of routes, including but not limited to systemic, intratumoral, intraperitoneal, parenteral, intravenous, intraarterial, intradermal, subcutaneous, intramuscular, intravitreal, sub-retinal, oral and nasal. The medicaments and compositions may be formulated in fluid or solid form. Fluid formulations may be formulated for administration by injection to a selected region of the human or animal body.

The extracellular vesicle may comprise a tag that binds to a molecule on the surface of the cell or tissue to be treated. The tag may specifically bind to the cell or tissue to be treated. The extracellular vesicle may comprise a therapeutic cargo. The therapeutic cargo may be a non-endogenous substance for interacting with a target gene in a target cell.

Extracellular vesicles may be administered alone or in combination with other treatments, either simultaneously or sequentially dependent upon the condition to be treated.

Extracellular vesicles loaded with a cargo as described herein may be used to deliver that cargo to a target cell. In some cases, the method is an in vitro or ex vivo method. In other cases the method is an in vivo method. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

Kit

Also disclosed herein are kits comprising extracellular vesicles. The kit may comprise one or more components selected from one or more extracellular vesicles, a nucleic acid such as an expression vector, DNA minicircle, plasmid or RNA, and a transfection reagent such as PEIMax. The kit may further comprise instructions and/or buffers and/or reagents suitable for use in the methods described herein.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1

We describe a method for the efficient in vitro and in vivo delivery of DNA and other nucleic acids by extracellular vesicles such as red blood cell extracellular vesicles (RBCEVs). We found that GFP-encoding DNA minicircles (MCs), although much larger in size and molecular weight as compared to GFP-encoding mRNA, can be loaded into RBCEVs at a higher efficiency and delivered more effectively to cells as compared to GFP mRNA. In addition, we found that DNA delivery is a unique feature of RBCEVs and is highly inefficient when attempted using exosomes.

Whilst not bound by theory, we hypothesize that this ability to load large DNA cargoes could be attributed to the unique membrane characteristics of RBCEVs. It has been reported that RBCEVs exhibit a bending modulus that is close to the highly flexible RBC membrane (Vorselen et al., Nature Communications 9, 4960 (2018)). On the other hand, exosomes are highly rigid vesicles due to the high concentration of lipid rafts enriched in cholesterol, gangliosides and sphingomyelin on their membranes (He et al., Theranostics., Exosome Theranostics: Biology and Translational Medicine. 2018; 8(1): 237-255). This evidence suggests possible structural differences between RBCEV and exosome membranes, which could account for their differential abilities to be loaded with DNA cargoes. We also showed that a systemically injected bolus of DNA loaded RBCEVs led to long term gene expression in the mouse, demonstrating that the RBCEV/DNA composition serves as a novel non-viral gene therapy entity and potentially bypassing the limitations associated with today's most advance gene therapy vectors such as AAVs.

As described below, we observed that RBCEVs loaded with minicircle DNA (MC) transfected more cells than RBCEVs loaded with mRNAs. This effect was irrespective of the loading method used, with MC transfecting more efficiently than mRNAs, when either electroporation or chemical transfection was used as the loading method. Our data suggest that DNA minicircles could be loaded at higher efficiency than mRNA, and delivered more effectively to target cells.

We also observed that RBCEVs loaded using chemical transfection were more effective at transducing cells than RBCEVs loaded using electroporation. This is the case whether the nucleic acid was mRNA or DNA minicircles. These data suggest that that our chemical transfection method resulted in higher levels of cargo than electroporation. Interestingly, by loading RBCEVs twice with cargo, cells were transfected much more efficiently than RBCEVs loaded only once.

Interestingly, although there is much literature around the potential to use exosomes to deliver nucleic acids, and particularly siRNA to target cells, our data suggests that RBCEVs loaded with MC transfect more cells than exosomes loaded with MCs. These data support the clinical use of RBCEVs as a nucleic acid delivery vehicle, as RBCEVs can be purified in large amounts from donor blood, can be readily loaded with large amounts of large-sized nucleic acids (DNA expression vectors and mRNA), previously thought to be impossible for EVs in general and are non-immunogenic.

Methods

Materials and Reagents

GFP mRNA was purchased from TriLink Biotechnologies and GFP and luciferase minicircle DNA (MCs) was produced using the MC-Easy Kit (System Biosciences). Human bone marrow-derived mesenchymal stem cell exosomes (MSC-exo) were purchased from System Biosciences (SBI). 293T cells were purchased from ATCC and cultured in Dulbecco's Modified Eagle's Medium containing 10% fetal bovine serum, in a 37° C. $CO_2$ incubator.

Purification and Quantification of EVs from Human RBCs and MSCs

Whole blood samples were obtained through Innovative Research, Inc from healthy donors with informed consents. RBCs were separated from plasma and white blood cells by using centrifugation and leukodepletion filters (Terumo Japan). Isolated RBCs were diluted in PBS and treated with 10 mM calcium ionophore (Sigma-Aldrich) overnight. To purify EVs, RBCs and cell debris were removed by centrifugation at 600 g for 20 min, 1600 g for 15 min, 3700 g for 15 min, and 10,000 g for 30 min at 4° C. The supernatants were passed through 0.45 µm filters. EVs were washed with 4 diavolumes of PBS and concentrated by tangential flow filtration (Pall Minimate), followed by further concentration using the 100 kD MWCO Amicon Ultra Centrifugal Units (Merck Millipore). Purified RBCEVs were stored at −80° C. EVs were quantified by assessing their hemoglobin content using the Hemoglobin Assay Kit (Abcam).

Nucleic Acid Loading of RBCEVs

Electroporation of RBCEVs was performed using a GenePulser Xcell electroporator (BioRad), exponential program at a fixed capacitance of 150 µF with 0.4 cm cuvettes. 75 µg RBCEVs were diluted in OptiMEM (ThermoFisher Scientific) containing 4% trehalose and mixed with 1.5 µg of GFP MCs or GFP mRNA to a total volume of 200 µl. An aliquot of 100 µl EV mixture was added to each cuvette and incubate on ice for 10 min. Electroporation was performed at 400 V.

In some experiments, 1 µg of mRNA or DNA was added to 5-7 µl of chemical-based transfection reagent (PEI Max (Polysciences, Inc.), a linear polyethyleneimine hydrochloride (MW 40,000)) in Opti-MEM (ThermoFisher) and incubated at room temperature for 10 min to facilitate complex formation. The mixture was added to 50 µg of washed RBCEVs and mixed gently. The reaction was incubated at 37° C. for 30 min with rotation, followed by ice for 10 min. Thereafter, loaded RBCEVs were pelleted at 21,000×g and washed twice with PBS. For experiments involving comparison with MSC-exo, MSC-exo was loaded with DNA in the same manner as described above, and for consistency both loaded RBCEVs and MSC-exo were purified with ExoQuick-TC (SBI) according to the manufacturer's instructions.

Assessment of Copy Number of Loaded Nucleic acids in RBCEVs qRT-PCR and qPCR were performed on known amounts of mRNA and DNA respectively, and Ct values were plotted against copy number to generate standard curves. Total RNA from mRNA-loaded RBCEVs was extracted using Trizol (ThermoFisher) and were converted to cDNA using the qScript cDNA Synthesis Kit (Quantabio) following the manufacturer's protocol. Total DNA from DNA MC-loaded RBCEVs was extracted using the DNeasy Blood and Tissue Kit (Qiagen). qPCR was performed on the cDNA/DNA samples to determine copy number. RBCEVs were quantified by ZetaView (Particle Metrix) based on the principles of Nanoparticle Tracking Analysis.

Flow Cytometry Analysis

Flow cytometry of cells in FACS buffer (PBS containing 0.5% fetal bovine serum) was performed using MACSQuant Analyzer 10 (Miltenyi Biotec) and analyzed using Flowjo V10 (Flowjo, USA). 293T cells were initially gated based on FSC-A and SSC-A to exclude the debris and dead cells (low FSC-A). The cells were further gated based on FSC-width vs. FSC-height, to exclude doublets and aggregates. Subsequently, the GFP-positive cells were gated in the FITC channel using untreated cells as controls, and the percentage of GFP-positive cells and mean fluorescence intensities were assessed.

Serum Stability of DNA-Loaded RBCEVs

RBCEVs were loaded with MCs using transfection reagent as described. 1-1.2 mL of whole blood was collected from 6-week old female Balb/C mouse through cardiac puncture. Serum was isolated by centrifugation of clotted whole blood at 3,000 g for 10 min. Serum or control (PBS) treatment was carried out by incubating 100 µL serum or PBS with 80 µg of MCs, or equivalent amount of transfection reagent-complexed MCs, or loaded RBCEVs for 2 h at 37° C. with agitation. After incubation, loaded RBCEVs were spun down at 21,000 g for 30 min to collect the pellet and supernatant. EDTA was added to all serum-treated samples to final concentration of 5 mM. Samples with EDTA were heated at 75° C. for 5 min to deactivate DNAse. Samples and DNA standards were mixed with DNA loading dye and loaded onto 1% agarose gel for electrophoresis.

Systemic In Vivo Administration of DNA-Loaded RBCEVs

All animal experiments were performed in accordance to experimental protocols approved by the Institutional Animal Care and Use Committee at the A*STAR Biological Resource Centre, Singapore. 6-week old female BALB/c or NSG mice were purchased from The Jackson Laboratory (ME, US). RBCEVs were loaded with luciferase-encoded plasmids by chemical transfection. Amount of DNA loaded in RBCEVs was quantified by gel densitometry. Unloaded controls and DNA-loaded RBCEVs were administered systemically in a single 200 µl bolus by tail vein injection. To detect the expression of luciferase, whole body bioluminescent images were captured at the indicated timepoints using the IVIS Spectrum system (PerkinElmer), 15 min following i.p. injection of 150 mg/kg D-luciferin (PerkinElmer). The visual output represents the total number of photons emitted per second as a false color image where the maximum is red and the minimum is dark blue.

Results

DNA Delivery by RBCEVs was More Efficient as Compared to mRNA

Figure 1B:
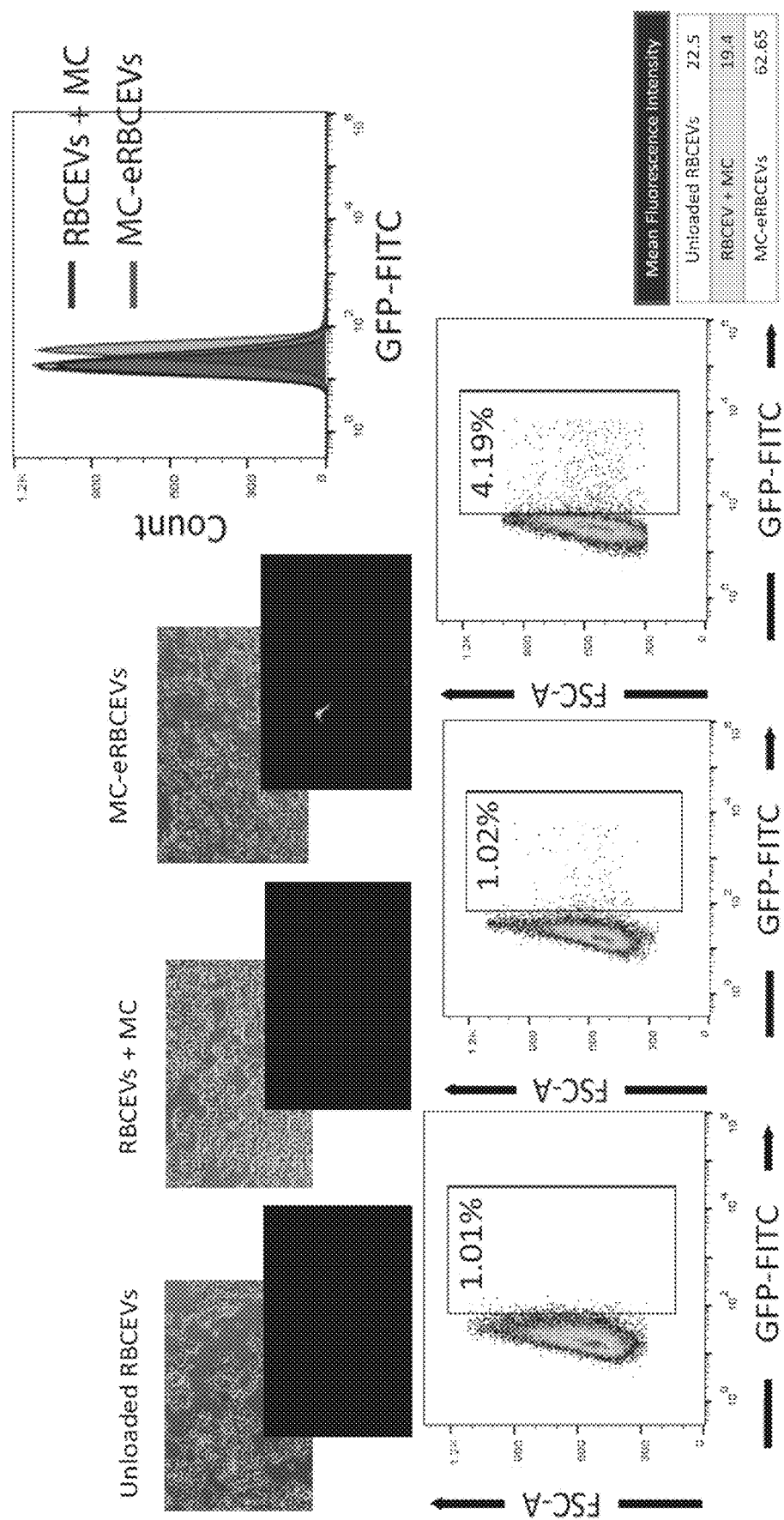

We assessed the ability of RBCEVs to be loaded with the 2 main classes of nucleic acids, circular double-stranded DNA (minicircles, MCs) and linear single-stranded mRNA. GFP MCs (2000 bp) and GFP mRNA (1000 bases) were assessed for their loading efficiencies in RBCEVs by electroporation. In this comparison, the MCs (dsDNA) are ~4× larger in molecular weight as compared to mRNA (ssRNA). Therefore, in principle, it should be more challenging to load the larger MC payload into RBCEVs. GFP MCs and GFP mRNA were loaded into RBCEVs by electroporation. We observed that in cells that were treated with mRNA-loaded RBCEVs, GFP expression levels were not high enough to be detected by flow cytometry (FIG. 1a). However, in cells treated with DNA MC-loaded RBCEVs, ~3% of the cells were positive for GFP (FIG. 1b).

Figure 2:
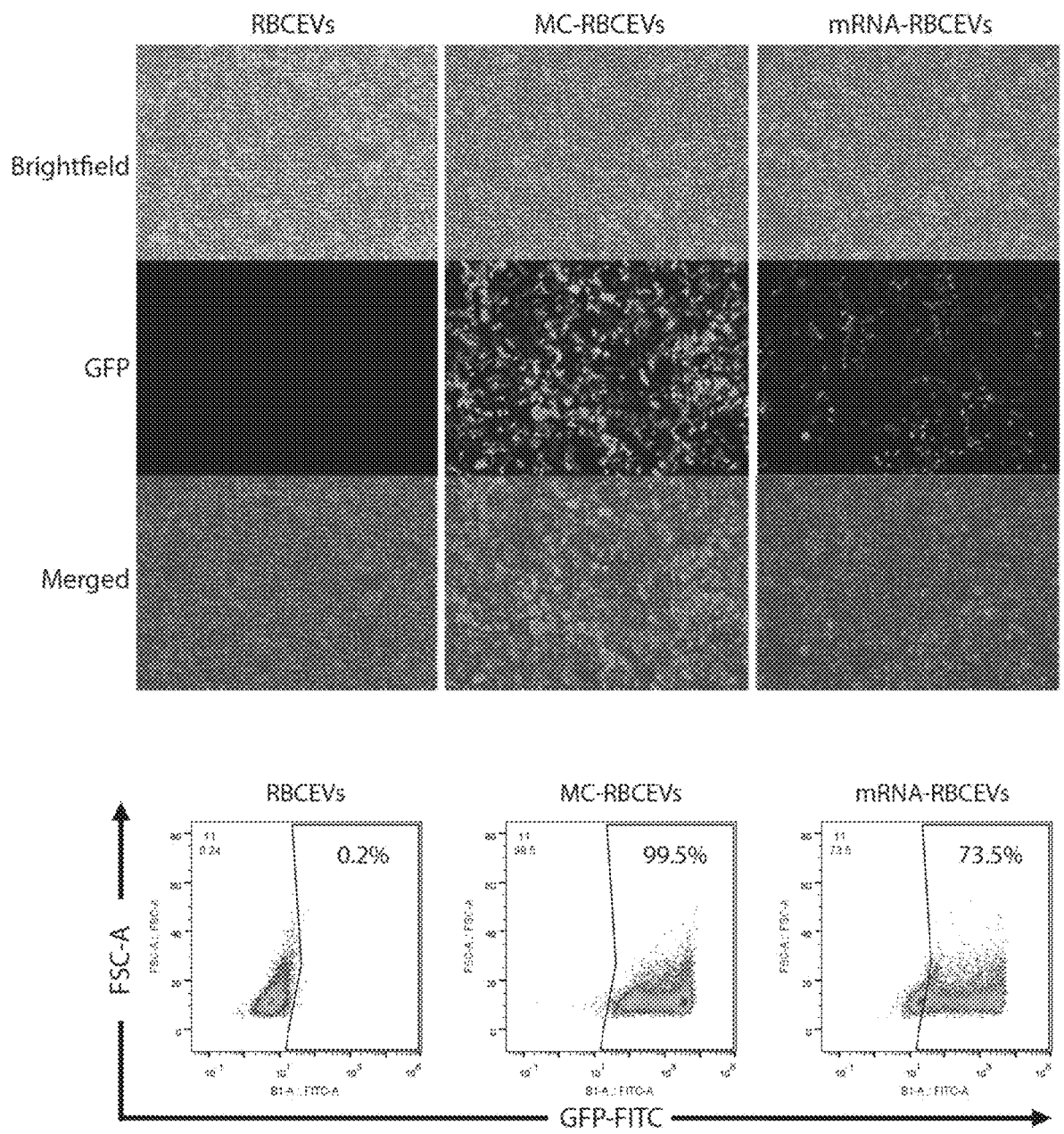
FIG. 2. Delivery of mRNA vs DNA into 293T cells by chemically-transfected RBCEVs. RBCEVs were chemically loaded with minicircle DNA (MC) or mRNA encoding GFP and treated to 293T cells. After 48 h, cells were imaged by microscopy and GFP-positive cells were quantified using flow cytometry. Percentage of GFP-positive cells are indicated in the scatter plots.

We also chemically transfected RBCEVs with DNA and mRNA prior to treating them to cells in vitro. As illustrated in FIG. 2a, using this method of cargo loading, we managed to load more copies of DNA into RBCEVs, as compared to mRNA. By dividing the total number of copies of cDNA measured by qPCR against the total number of EV particles measured by nanoparticle tracking analysis, we calculated that 1.16 copies of GFP mRNA were loaded into each vesicle, which is significantly less as compared to 3.74 copies of GFP DNA MCs loaded per vesicle (data not shown). When treating 293T cells with these loaded vesicles, we observed a larger percentage of cells becoming positive for green fluorescence at 48 hours when cells were treated with DNA MC cargo as compared to mRNA cargo (99.5% vs 73.5%, FIG. 2).

RBCEVs are Better Delivery Vehicles for DNA Cargoes as Compared to MSCEVs

Figure 3A:
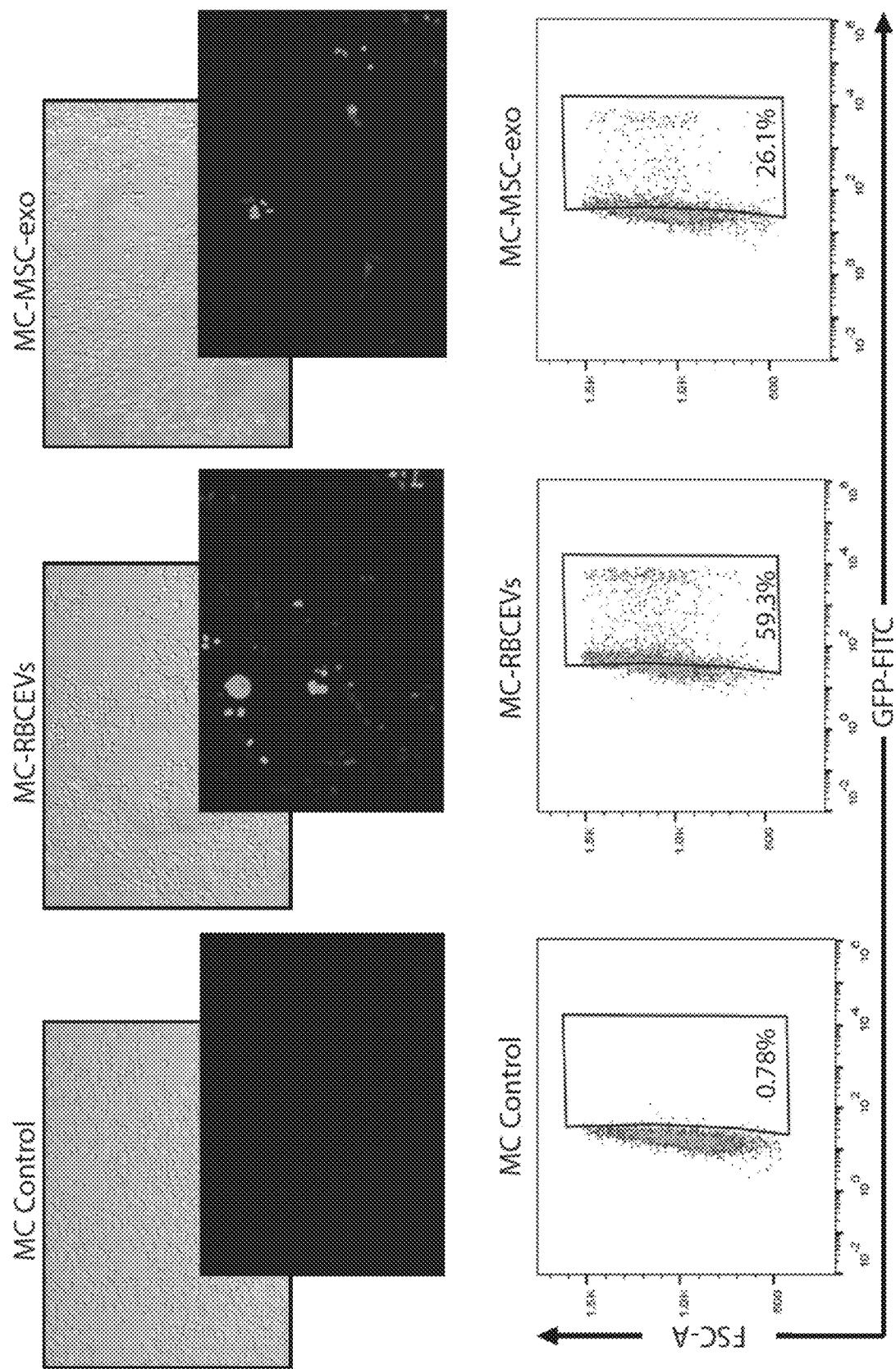
FIGS. 3A-3B. Comparison of DNA minicircle delivery between RBCEVs and MSC-exo.
Figure 3B:
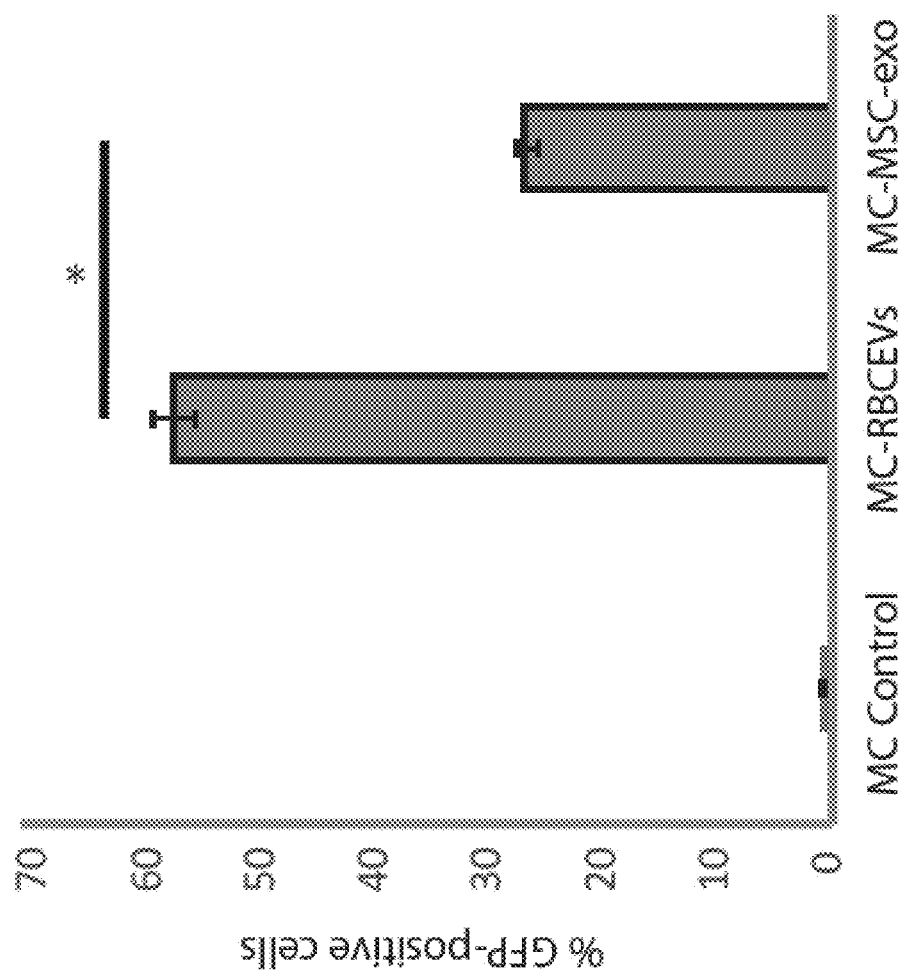

MSCs are prolific producers of exosomes and it is reported in the field that the exosomes produced by MSCs retain the immunomodulatory properties of the cells, and therefore these exosomes can be administered to patients allogenically. For these reasons, MSC-exo are actively being explored as a novel drug delivery vehicle for a wide variety of therapeutic payloads. However, several challenges accompany the clinical use of MSC-exo, such as extensive cell culture to obtain therapeutic human doses of EVs, and to date there has been little success in loading large nucleic acid payloads (mRNA or DNA expression vectors) into EVs in general, therefore limiting their application in gene delivery. We sought to compare the DNA loading capacity of RBCEVs against MSC-exo using the above-mentioned method of chemical transfection. An equal amount of RBCEVs and MSC-exo were loaded with the same amount of GFP-encoding DNA MCs and for consistency both types of vesicles were purified using ExoQuick. We found that 293T cells treated with DNA-loaded RBCEVs were 59.3% positive for GFP, as compared to 26.1% positive for DNA-loaded MSC-exo (FIGS. 3, a and b). This suggests that RBCEVs, given their safety and biocompatibility, the high yield obtainable from a single unit of blood, as well as their ease to be loaded with large nucleic acids, are an ideal non-viral gene therapy vehicle.

RBCEVs can Deliver DNA Cargo of a Wide Range of Sizes

Figure 7A:
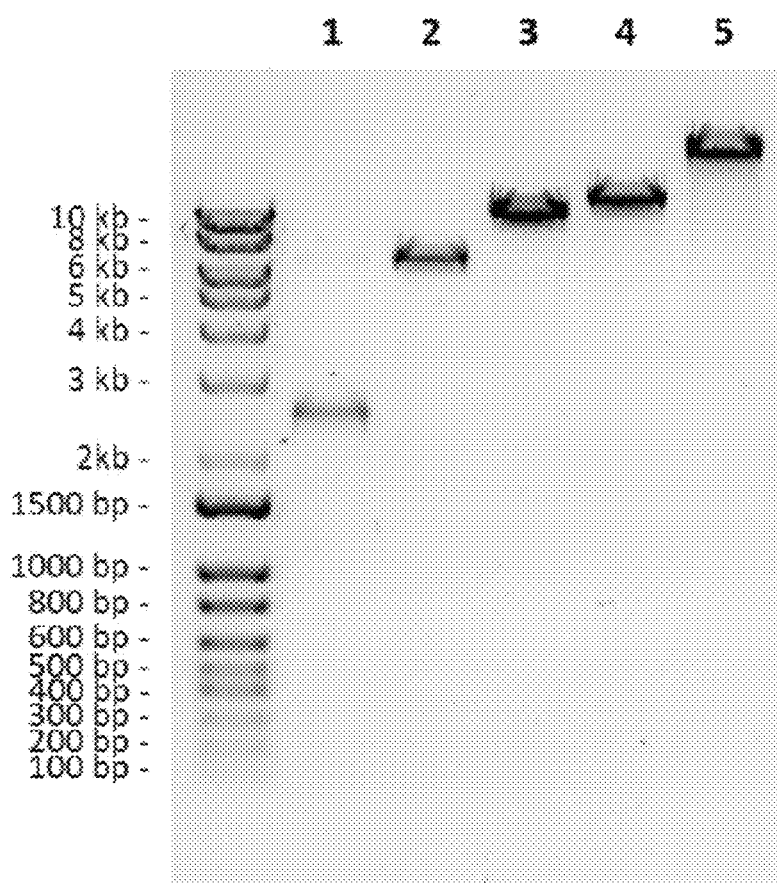
FIGS. 7A-7C. Assessing DNA cargo limitation of RBCEVs.
Figure 7B:
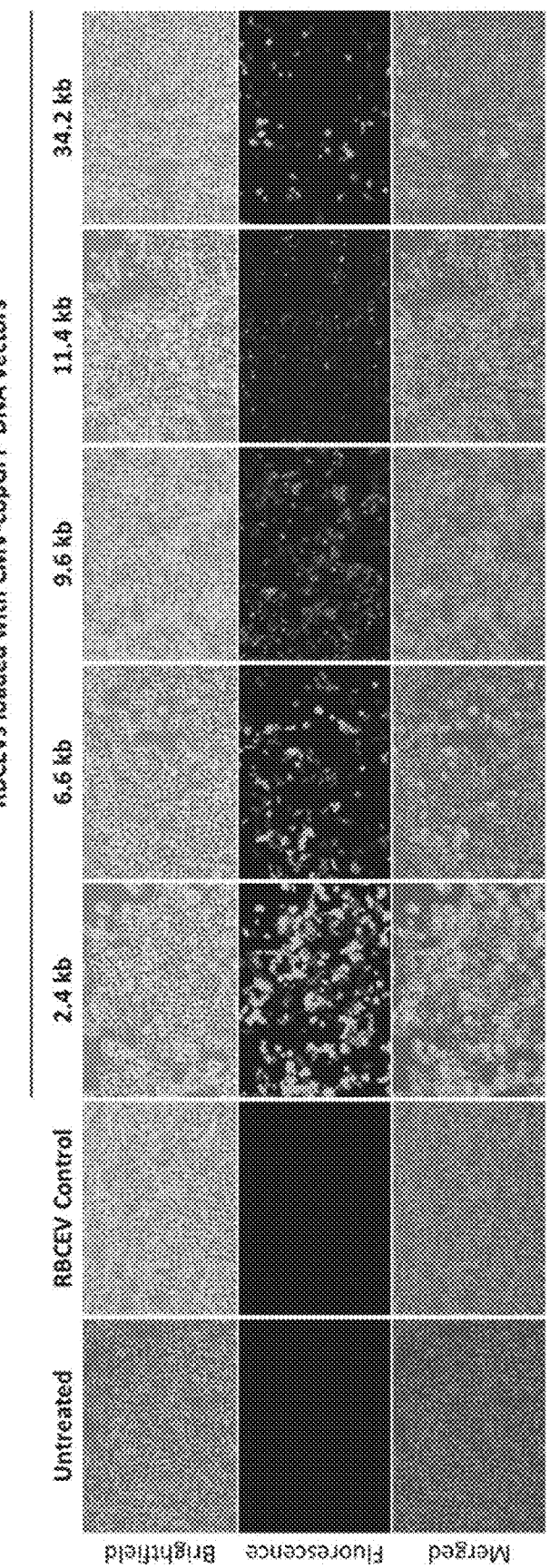
Figure 7C:
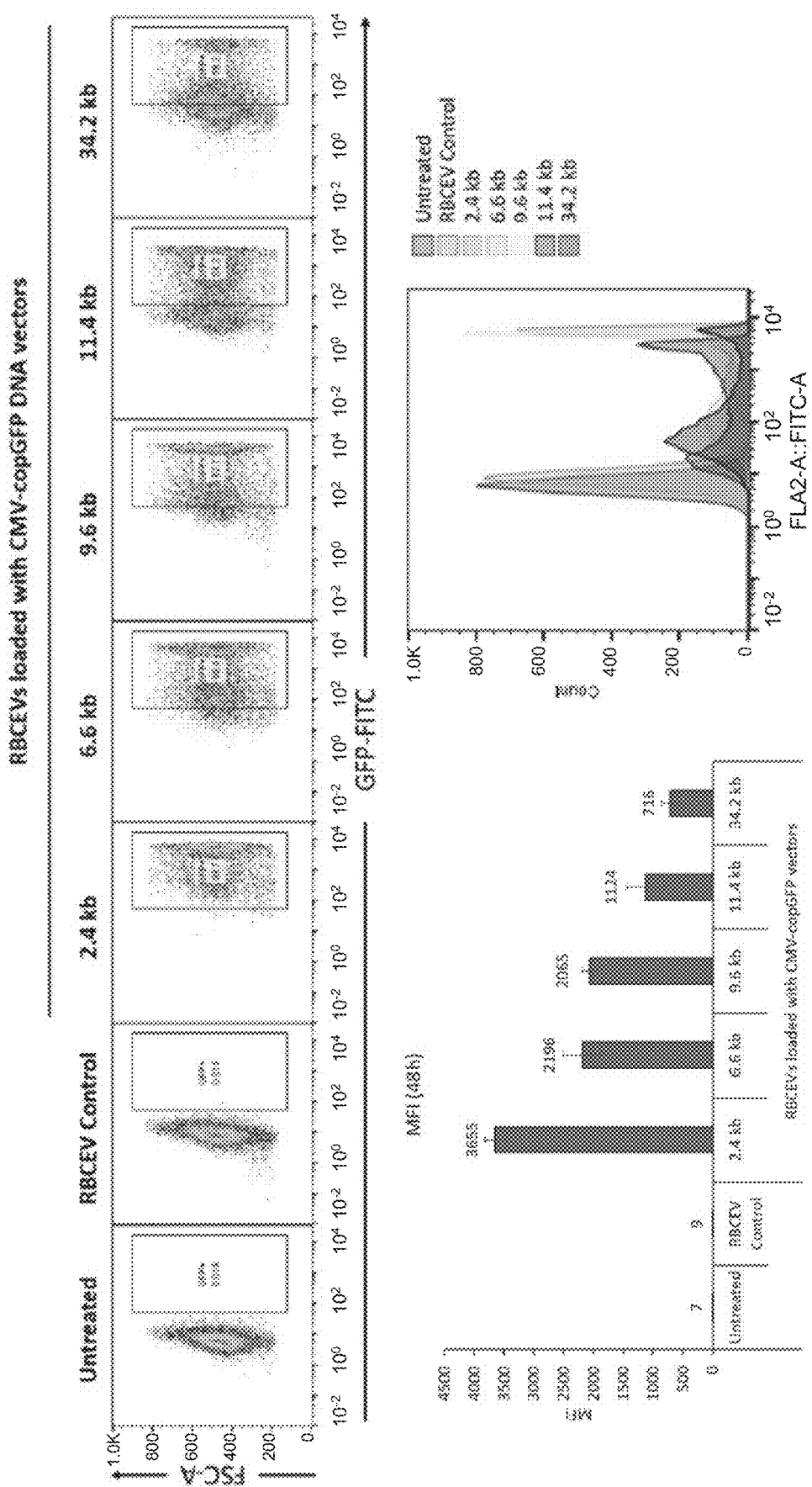
Figure 8:
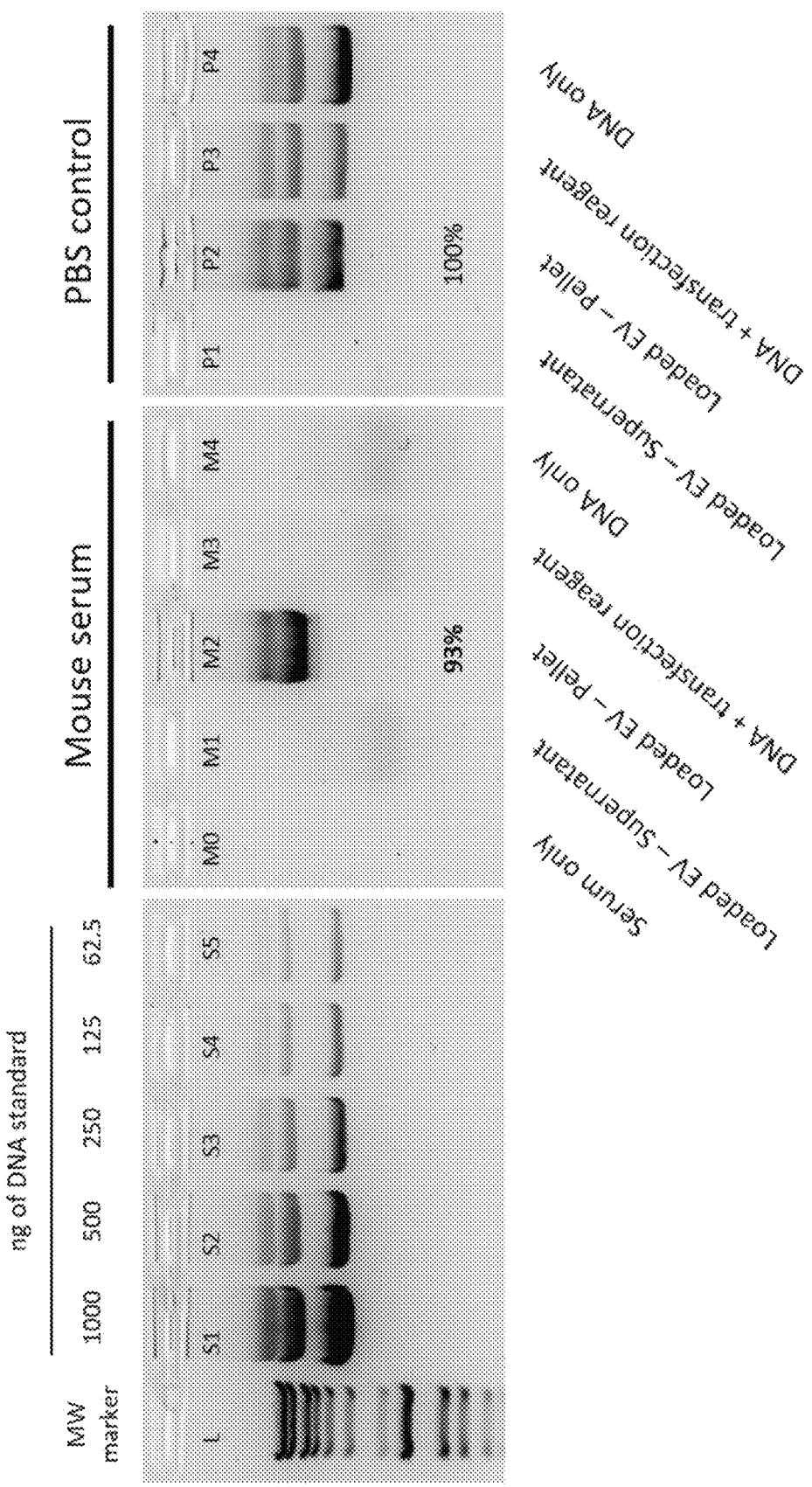
FIG. 8. Serum stability of DNA loaded in RBCEVs. Naked MCs (minicircles), MCs complexed with transfection reagent, and MCs loaded in RBCEVs were treated with mouse serum (M1 to M4) or PBS (P1 to P4). Serum alone was used as background control (M0). Percentage of DNA recovered was quantified by gel densitometry based on DNA mass-intensity standard curve (S1 to S5)

Gene therapy is mainly mediated by viral vectors, with AAV at the forefront of in vivo gene therapy. However, besides challenges with immunogenicity and manufacturing, one of the other limitations of using viral vectors is payload capacity. The capacity of the AAV genome is 4.7 kb and this greatly limits the size of the transgene that can be inserted. We sought to identify the size limit of DNA cargos that can be delivered by RBCEVs. Equal mass of DNA cargoes of various sizes (2.4, 6.6, 9.6, 11.4 and 34.2 kb—see FIG. 7a) each containing a single copy of copGFP transgene driven by the CMV promoter was chemically loaded into RBCEVs and equal amounts of loaded and washed RBCEVs were added to 293T cells in culture. 48 h later, cells were imaged by fluorescence microscopy followed by analysis using the flow cytometer. As depicted in FIG. 7b, successfully transfected fluorescent cells were observed for all DNA cargoes. Interestingly, the percentage of GFP-positive cells as well as the mean fluorescence intensity decreased with increasing sizes of the cargoes (99.7% positive cells for 2.4 kb cargo and decreasing down to 59.2% positive cells for 34.2 kb cargo), and this is likely a result of delivering an equal mass of DNA which contains different copy numbers of the payload depending on its size (FIGS. 7b and 7c). Nevertheless, results suggest that RBCEVs can deliver DNA cargoes of a wide range of sizes.

RBCEVs Protect Loaded DNA from Serum Degradation

Figure 5A:
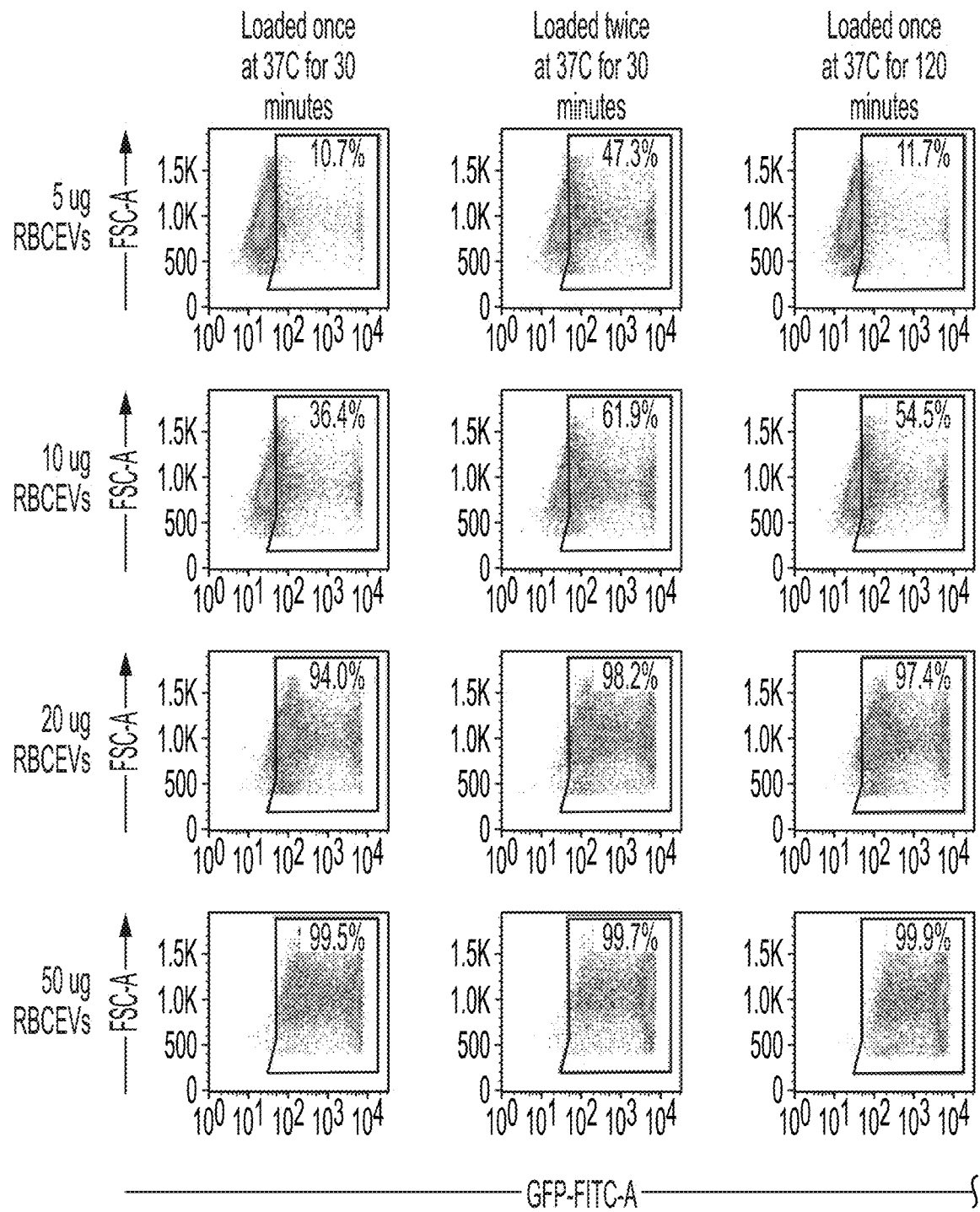
FIGS. 5A-5B. Comparison of two different optimization parameters. Unloaded RBCEVs were mixed with GFP minicircles and transfection reagent for 30 minutes or 120 minutes, either once or twice. 5 μg, 10 μg, 20 μg or 50 μg of the RBCEVs were then added to 293T cells. After 48 h, GFP positive cells were quantified using flow cytometry. Percentage of GFP-positive cells are indicated in the scatter plots.
Figure 5B:
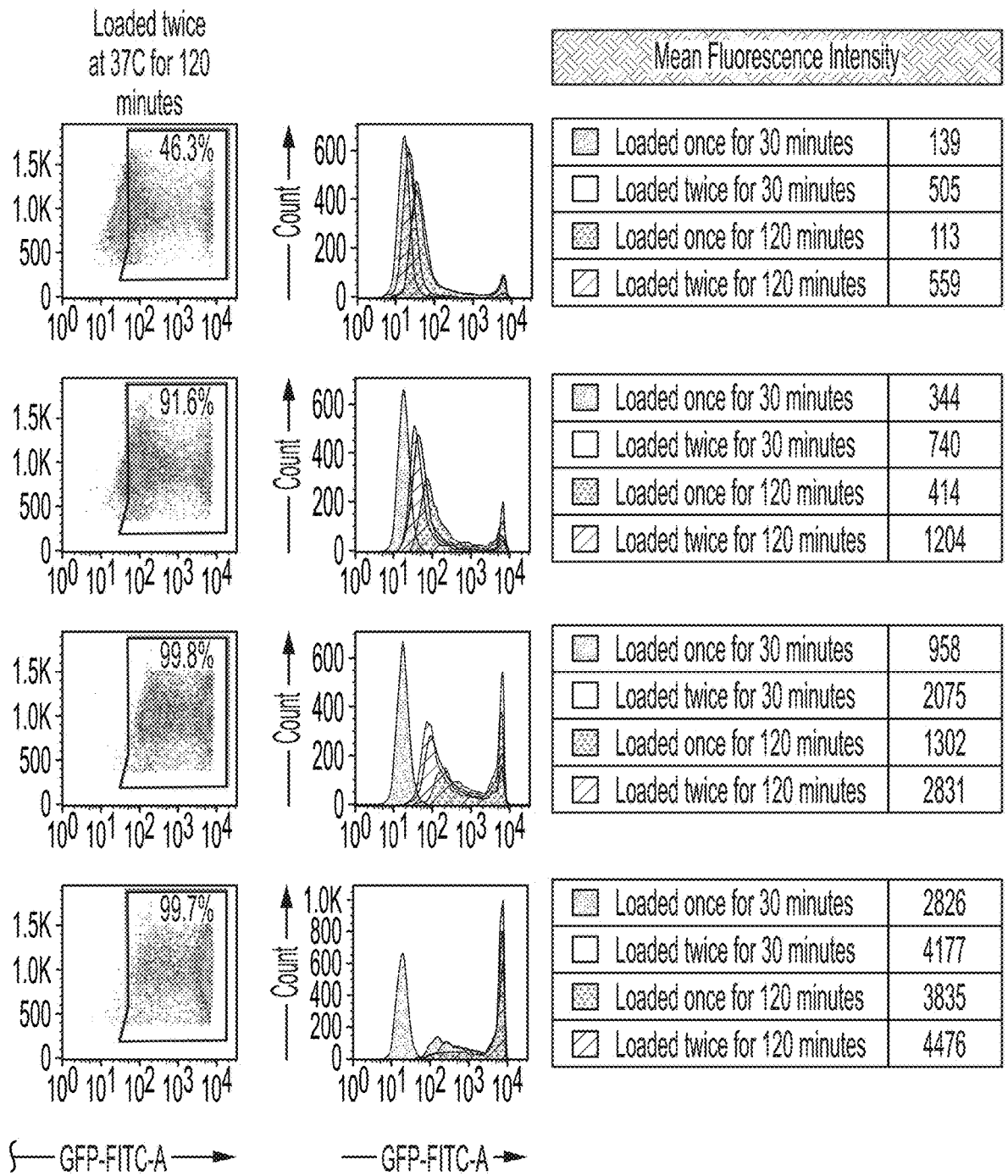
Figure 6:
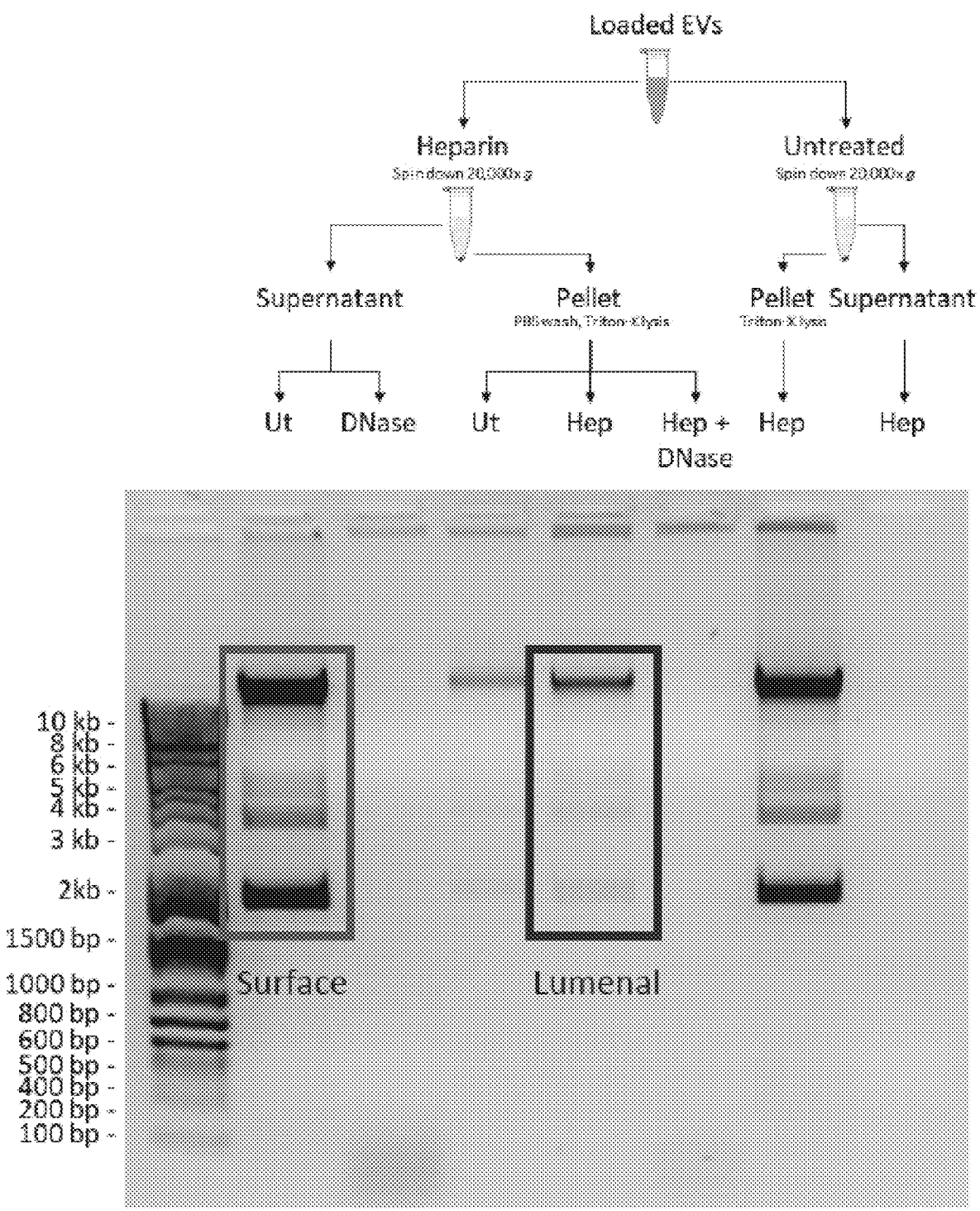
FIG. 6. Assessment of the location of DNA in the loaded RBCEVs. Untreated DNA-loaded RBCEVs were centrifuged at 20,000×g. Electrophoresis of the supernatant fraction and Triton-X lysed pellet fractions were run on SDS-PAGE gel indicated that DNA was isolated in the pellet fraction, indicating that the RBCEVs were loaded with DNA. When the DNA-loaded RBCEVs were pre-treated with heparin to dissociate DNA from PEI-Max, DNA was isolated in both the supernatant and pellet fraction, indicating both external and lumenal loading of the RBCEVs. Treatment of the lysed pellet fraction with further heparin indicated that the internalised DNA was present in complex with PEI-Max.

For applications involving systemic administration of DNA-loaded RBCEVs, it is important to ensure that the loaded DNA cargo is stable to the activity of nucleases in the circulation. Hence, we assessed the stability of loaded DNA by treating MCs, MCs complexed with transfection reagent, and MC-loaded RBCEVs with serum from Balb/C mice and analyzed residual DNA using gel electrophoresis (FIG. 5). As observed in lane M0, there is no contaminating DNA from the serum sample used. DNAse in the serum was able to degrade not only naked DNA (lane M4), but also DNA complexed with transfection reagent (lane M3). Neither naked DNA nor DNA complexed with transfection reagent was observed in PBS-treated controls (lanes P4 and P3 respectively). However, even after serum incubation, loaded RBCEVs retained 93% of intact DNA payload when compared to PBS-treated control (lanes M2 vs P2). This suggests that RBCEVs were able to protect DNA payload from serum nuclease degradation and can be administered systemically without any concerns on serum stability.

In Vivo Delivery of DNA Cargo for Long Term Gene Expression in Mice

Figure 4:
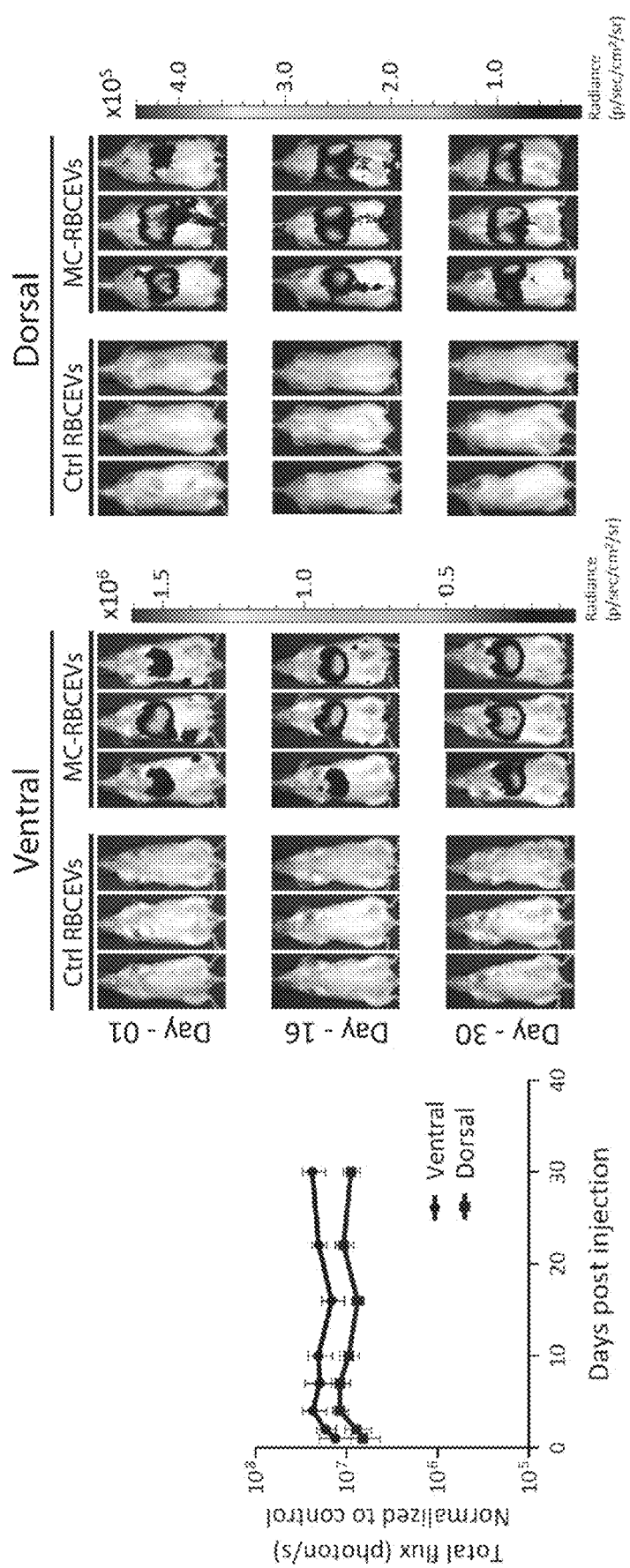
FIG. 4. Evaluation of in vivo gene expression in mice following injection of DNA-loaded RBCEVs. 6-week old female NSG mice were administered with unloaded RBCEVs (n=3) or luciferase-encoding MC-loaded RBCEVs (n=3) via tail vein injection on Day 0. Luciferase activity was assessed over time by whole body bioluminescence imaging following the injection of luciferin substrate, at timepoints indicated by the x-axis. Representative ventral and dorsal images of the mice at the indicated timepoints are shown on the right.
Figure 9A:
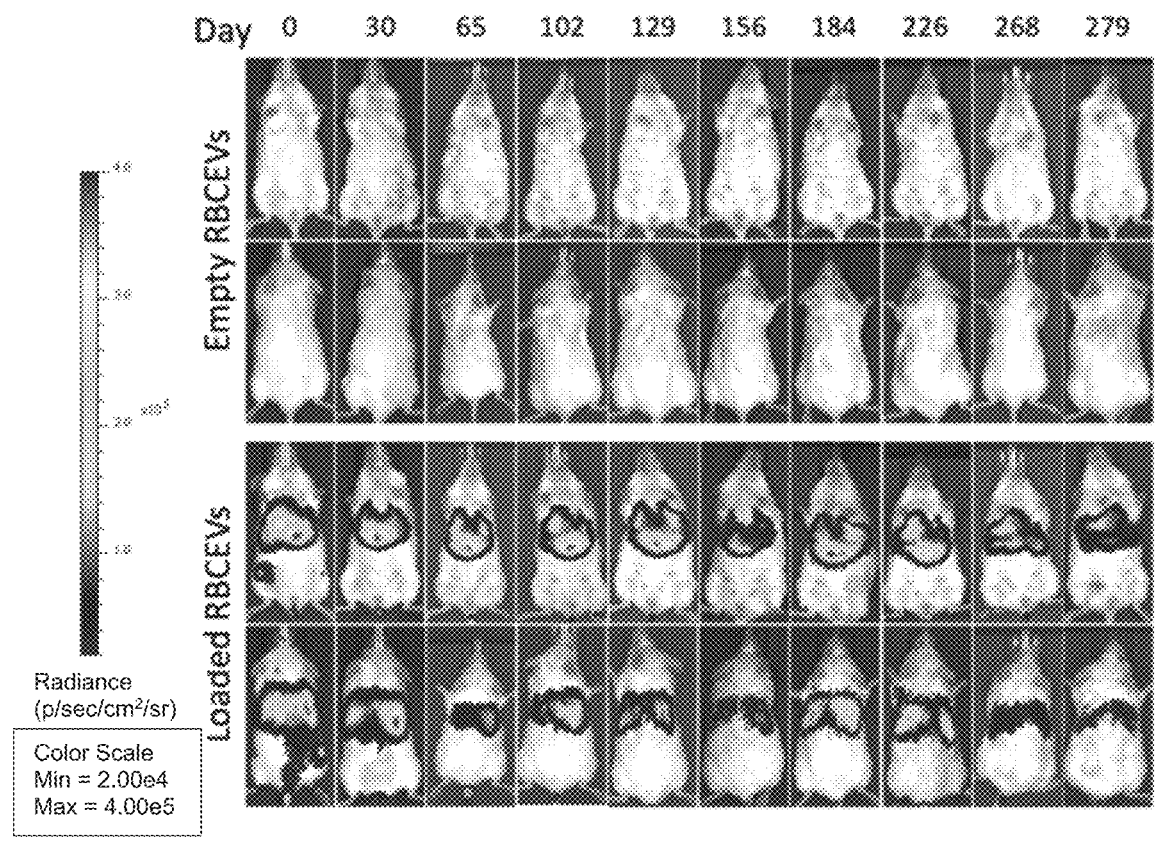
FIGS. 9A-9B. Evaluation of in vivo gene expression in mice following injection of DNA-loaded RBCEVs.
Figure 9A:
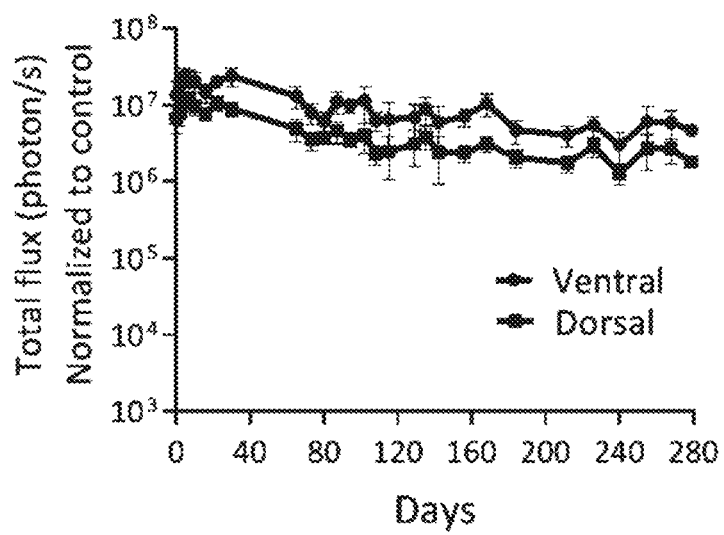

One of the key features for a gene therapy vehicle is the ability to deliver genes in vivo and confer sustained, long term gene expression in the target tissue. To demonstrate this, we injected luciferase-encoded DNA-loaded RBCEVs into the tail vein of NSG mice, at a DNA dose of 2 mg/kg. Kinetics of whole body luciferase expression was monitored using the IVIS Spectrum bioluminescence imager. RBCEV-mediated delivery to cells in vivo led to sustained, long term luciferase activity in the torso region of the mice. Bioluminescent signal was monitored over 30 dpi (45 dpi to date) without any observable reduction (FIG. 4) and over 279 days with minimal reduction (FIG. 9a).

Figure 9B:
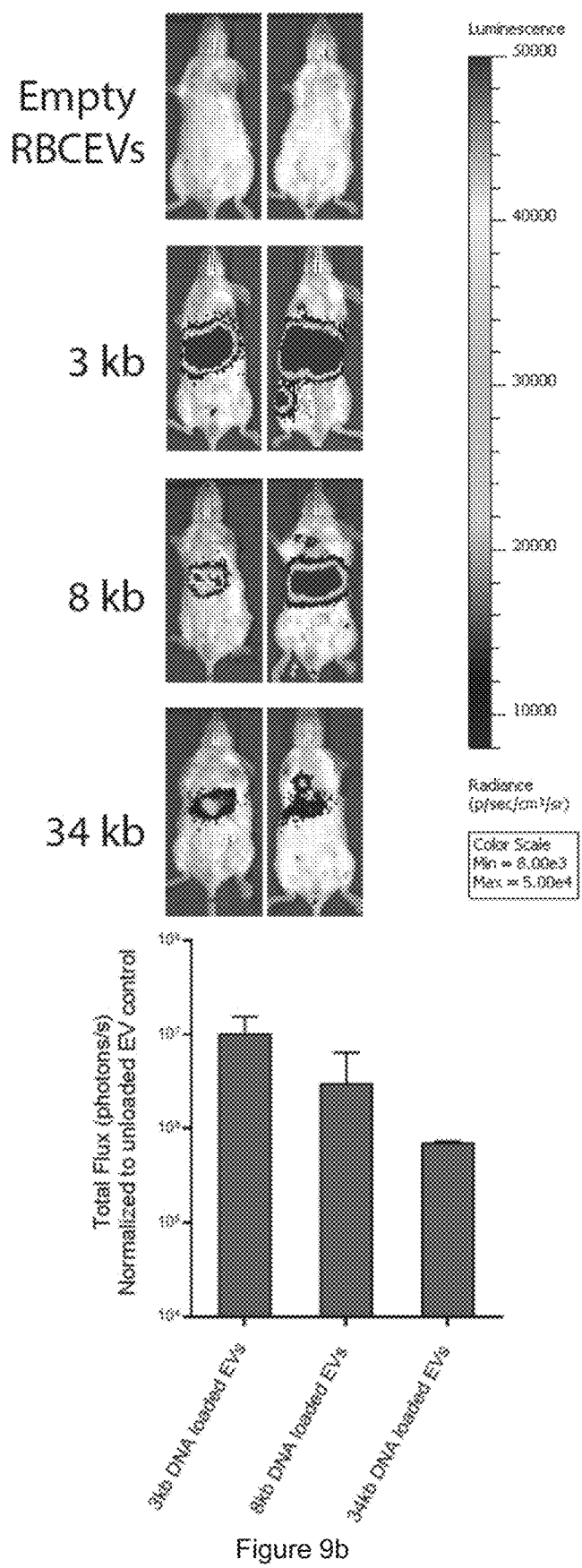

To demonstrate the potential to deliver large DNA cargoes in vivo, RBCEVs loaded with 3 kb, 8 kb, and 34 kb luciferase-encoded DNA cargoes were systemically administered into the tail veins of BALB/c mice at an equal DNA dose of 2.5 mg/kg. Irrespective of the size of the DNA cargoes, all the mice injected with DNA-loaded RBCEVs displayed luminescence at 48 h timepoint (FIG. 9b). However, we did observe reduced transgene expression with increasing size of DNA cargoes, again attributed to different copy numbers of payload depending on its molecular weight. Taken together, we have demonstrated RBCEVs' ability to deliver large DNA cargoes and trigger long term transgene expression in mice, highlighting its potential to become a novel non-viral gene therapy vector.

REFERENCES

A number of publications are cited above in order to more fully describe and disclose the invention and the state of the art to which the invention pertains. Full citations for these references are provided below. The entirety of each of these references is incorporated herein by reference.

For standard molecular biology techniques, see Sambrook, J., Russel, D. W. *Molecular Cloning, A Laboratory Manual.* 3 ed. 2001, Cold Spring Harbor, N.Y.: Cold Spring Harbor Laboratory Press 1. Kanada et al., Differential fates of biomolecules delivered to target cells via extracellular vesicles. PNAS Mar. 24, 2015 112 (12) E1433-E1442; first published Feb. 23, 2015
2. Yang, Z., Shi, J., Xie, J. et al. Large-scale generation of functional mRNA-encapsulating exosomes via cellular nanoporation. Nat Biomed Eng (2019) doi:10.1038/s41551-019-0485-1
3. WO2010/119256
4. Lamichhane et al., Exogenous DNA Loading into Extracellular Vesicles via Electroporation is Size-Dependent and Enables Limited Gene Delivery. Mol Pharm. 2015 Oct. 5; 12(10): 3650-3657.
5. Usman et al., Efficient RNA drug delivery using red blood cell extracellular vesicles. Nature Communications Nat Commun 9, 2359 (2018) doi:10.1038/s41467-018-04791-8.
6. Wang et al., ASMMs as a versatile platform for intracellular delivery of macromolecules. Nature Communications 2018 9-960.

The invention claimed is:

1. A preparation comprising a population of red blood cell extracellular vesicles (RBCEVs) loaded with a DNA cargo and a cationic reagent, wherein:
   the RBCEVs have a size between 50 nm and 1,000 nm in diameter,
   the DNA cargo has a length between 2,000 bases and 40,000 bases;
   the cationic reagent complexes with the DNA cargo and is a polyethylenimine (PEI) reagent
   and further wherein the preparation is characterized in that:
   when the preparation is contacted with recipient mammalian cells, it is more effective at transfecting the mammalian cells with the DNA cargo than is an otherwise comparable reference preparation loaded by electroporation.

2. The preparation of claim 1 characterized in that, when contacted with recipient mammalian cells, it achieves transfection of more than 50% of the mammalian cells.

3. The preparation of claim 1 characterized in that it is at least twice as effective at transfecting the mammalian cells than is the reference preparation.

4. The preparation of claim 1, further characterized in that, when contacted with recipient mammalian cells, it transfects more cells than does an otherwise comparable reference preparation loaded with an RNA cargo, rather than the DNA cargo, and the cationic reagent.

5. The preparation of claim 1, wherein the DNA cargo is single-stranded (ssDNA).

6. The preparation of claim 1, wherein the DNA cargo is double-stranded (dsDNA) and has a length between 1,000 base pairs and 20,000 base pairs.

7. The preparation of claim 1, wherein the DNA cargo is an expression vector comprising a transgene encoding a protein or peptide.

8. The preparation of claim 1, wherein the DNA cargo is circular.

9. The preparation of claim 1, wherein the DNA cargo is a minicircle or plasmid.

10. The preparation of claim 1, wherein the DNA cargo is linear.

11. The preparation of claim 1, wherein the DNA cargo is loaded in the lumen of the RBCEVs.

12. The preparation of claim 1, wherein the RBCEVs are derived or obtained from mammalian red blood cells.

13. The preparation of claim 1, wherein the RBCEVs are isolated from a sample of human red blood cells.

14. The preparation of claim 1, wherein each RBCEV within the population is loaded with an average of at least 1.0 copy number of the DNA cargo, at least 2.0 copy numbers of the DNA cargo, at least 3.0 copy numbers of the DNA cargo, or at least 4.0 copy numbers of the DNA cargo.

15. The preparation of claim 1, wherein the PEI reagent is a linear polyethylenimine hydrochloride (LPH) having a molecular weight of 25,000 Da or 40,000 Da.

16. A method of loading a population of RBCEVs with a DNA cargo,
    which method comprises steps of:
    contacting the population of RBCEVs with a cationic reagent and the DNA cargo for a period of time sufficient for the DNA cargo to be loaded into RBCEVs of the population so that a loaded preparation is prepared,
    wherein the RBCEVs have a size between 50 nm and 1,000 nm in diameter;
    the DNA cargo has a length between 2,000 bases and 40,000 bases;
    the cationic reagent complexes with the DNA cargo and is a polyethylenimine (PEI) reagent; and further wherein the loaded preparation is characterized in that, when contacted with recipient mammalian cells, it is more effective at transfecting the mammalian cells with the DNA cargo than is an otherwise comparable reference preparation loaded by electroporation.

17. The method of claim 16, wherein the RBCEVs have a size between 100 nm and 300 nm in diameter.

18. The method of claim 16, wherein the loaded preparation is characterized in that it is at least twice as effective at transfecting the mammalian cells than is the reference preparation.

19. The method of claim 16, wherein the loaded preparation is characterized in that, when contacted with recipient mammalian cells, it achieves transfection of more than 50% of the mammalian cells.

20. The method of claim 16, wherein the loaded preparation is characterized in that, when contacted with recipient mammalian cells, it transfects more cells than does an otherwise comparable reference preparation loaded with an RNA cargo, rather than the DNA cargo, and the cationic reagent.

21. The method of claim 16, wherein the polyethylenimine (PEI) reagent is a linear polyethylenimine hydrochloride.

22. The preparation of claim 1, wherein the RBCEVs have a size between 100 nm and 300 nm in diameter.

* * * * *